(12) United States Patent
Faries, Jr.

(10) Patent No.: US 8,789,534 B2
(45) Date of Patent: Jul. 29, 2014

(54) METHOD AND APPARATUS FOR WARMING MEDICAL SOLUTIONS IN A THERMAL TREATMENT SYSTEM EMPLOYING A REMOVABLE BASIN

(75) Inventor: Durward I. Faries, Jr., Las Vegas, NV (US)

(73) Assignee: Patented Medical Solutions, LLC, Las Vegas, NV (US)

( * ) Notice: Subject to any disclaimer, the term of this patent is extended or adjusted under 35 U.S.C. 154(b) by 500 days.

(21) Appl. No.: 12/420,455

(22) Filed: Apr. 8, 2009

(65) Prior Publication Data

US 2009/0255540 A1 Oct. 15, 2009

Related U.S. Application Data

(60) Provisional application No. 61/043,415, filed on Apr. 9, 2008.

(51) Int. Cl.
*A61B 19/08* (2006.01)

(52) U.S. Cl.
USPC ............. 128/849; 236/1 C; 219/430; 219/433

(58) Field of Classification Search
USPC ........ 219/430, 433, 441, 442; 236/1 C, 93 R; 128/849
See application file for complete search history.

(56) References Cited

U.S. PATENT DOCUMENTS

| | | |
|---|---|---|
| 2,174,425 A | 9/1939 | Schlumbohm |
| 2,323,356 A | 7/1943 | Rosay |
| 2,599,192 A | 6/1952 | Miller |
| 2,613,511 A | 10/1952 | Walsh |
| 2,807,701 A | 9/1957 | Conlin et al. |
| 2,813,450 A | 11/1957 | Dzus |

(Continued)

FOREIGN PATENT DOCUMENTS

| | | |
|---|---|---|
| JP | 61-185967 | 11/1986 |
| JP | 06-123532 | 5/1994 |

OTHER PUBLICATIONS

PCT International Preliminary Report on Patentability and Written Opinion, (8 pages).

(Continued)

*Primary Examiner* — Patricia Bianco
*Assistant Examiner* — Camtu Nguyen
(74) *Attorney, Agent, or Firm* — Edell, Shapiro & Finnan, LLC

(57) ABSTRACT

A drape device is provided for use with a thermal treatment system, where the thermal treatment system includes a receptacle dimensioned to receive a basin, a heater to heat items placed within the receptacle and a limit switch that is operable to identify when the basin or other item is placed within the receptacle and to further activate the heater upon identification by the limit switch of the basin or other item being placed within the receptacle. The drape device includes a drape that can be placed within the receptacle to provide a barrier between items placed on the drape and the receptacle. The drape device further includes engaging structure configured to engage the drape and one of the basin and the receptacle. In one embodiment, the engaging structure includes an actuation member that facilitates operation of the limit switch and activation of the heater without the use of the basin. In another embodiment, the engaging structure is securable to the basin to facilitate securing of the drape within the basin during use of the thermal treatment system.

35 Claims, 14 Drawing Sheets

(56) References Cited

U.S. PATENT DOCUMENTS

| | | |
|---|---|---|
| 3,249,070 A | 5/1966 | Day et al. |
| 3,519,979 A | 7/1970 | Bodenstein |
| 3,869,596 A | 3/1975 | Howie |
| 3,902,484 A | 9/1975 | Winters |
| 4,053,954 A | 10/1977 | Chapman |
| 4,242,932 A | 1/1981 | Barmore |
| 4,270,067 A | 5/1981 | Thomas et al. |
| 4,284,880 A | 8/1981 | Keiser |
| 4,393,659 A | 7/1983 | Keyes et al. |
| 4,458,139 A | 7/1984 | McClean |
| 4,474,016 A | 10/1984 | Winchell |
| 4,522,041 A | 6/1985 | Menzel |
| 4,569,259 A | 2/1986 | Rubin et al. |
| 4,625,098 A | 11/1986 | Joe |
| 4,782,835 A | 11/1988 | Bernardini |
| 4,828,876 A | 5/1989 | Ohhara et al. |
| 4,869,271 A | 9/1989 | Idris |
| 4,903,710 A | 2/1990 | Jessamine et al. |
| 4,934,152 A | 6/1990 | Templeton |
| 4,953,269 A | 9/1990 | Ragsdale |
| 4,967,061 A | 10/1990 | Weber, Jr. et al. |
| 5,040,699 A | 8/1991 | Gangemi |
| 5,042,455 A | 8/1991 | Yue et al. |
| 5,042,981 A | 8/1991 | Gross |
| 5,129,033 A | 7/1992 | Ferrara et al. |
| 5,163,299 A | 11/1992 | Faries, Jr. et al. |
| 5,174,306 A | 12/1992 | Marshall |
| 5,310,524 A | 5/1994 | Campbell et al. |
| 5,331,820 A | 7/1994 | Faries, Jr. et al. |
| 5,333,326 A | 8/1994 | Faries, Jr. et al. |
| 5,345,063 A | 9/1994 | Reusche et al. |
| 5,351,675 A | 10/1994 | Brodsky |
| 5,363,746 A | 11/1994 | Gordon |
| 5,374,813 A | 12/1994 | Shipp |
| 5,383,476 A | 1/1995 | Peimer et al. |
| 5,386,835 A | 2/1995 | Elphick et al. |
| 5,396,905 A | 3/1995 | Newman et al. |
| 5,400,267 A | 3/1995 | Denen et al. |
| 5,400,616 A | 3/1995 | Faries, Jr. et al. |
| 5,402,644 A | 4/1995 | Faries, Jr. et al. |
| 5,429,801 A | 7/1995 | Faries, Jr. et al. |
| 5,435,322 A | 7/1995 | Marshall |
| 5,443,082 A | 8/1995 | Mewburn |
| 5,449,892 A | 9/1995 | Yamada |
| 5,457,962 A | 10/1995 | Faries, Jr. et al. |
| 5,463,213 A | 10/1995 | Honda |
| 5,480,302 A | 1/1996 | Fife |
| 5,502,980 A | 4/1996 | Faries, Jr. et al. |
| 5,517,170 A | 5/1996 | Peters |
| 5,522,095 A | 6/1996 | Faries, Jr. et al. |
| 5,522,805 A | 6/1996 | Vancaillie et al. |
| 5,524,478 A | 6/1996 | Joy et al. |
| 5,524,643 A * | 6/1996 | Faries et al. ............ 128/849 |
| 5,531,697 A | 7/1996 | Olsen |
| 5,539,185 A | 7/1996 | Polster |
| 5,549,543 A | 8/1996 | Kim |
| 5,551,240 A * | 9/1996 | Faries et al. ............ 62/3.6 |
| 5,615,423 A | 4/1997 | Faries, Jr. et al. |
| 5,653,938 A | 8/1997 | Faries, Jr. et al. |
| 5,658,478 A | 8/1997 | Roeschel et al. |
| 5,664,582 A | 9/1997 | Szymaitiz |
| 5,666,831 A | 9/1997 | Doros |
| 5,715,547 A | 2/1998 | Becker et al. |
| 5,717,188 A | 2/1998 | Vaillancourt |
| 5,800,352 A | 9/1998 | Ferre et al. |
| 5,809,788 A | 9/1998 | Faries, Jr. et al. |
| 5,816,252 A | 10/1998 | Faries, Jr. et al. |
| 5,857,467 A | 1/1999 | Faries, Jr. et al. |
| 5,862,672 A | 1/1999 | Faries, Jr. et al. |
| 5,879,621 A | 3/1999 | Faries, Jr. et al. |
| 5,913,650 A | 6/1999 | Daoud |
| 5,950,438 A | 9/1999 | Faries, Jr. et al. |
| D417,809 S | 12/1999 | Hofman |
| 6,003,328 A | 12/1999 | Faries, Jr. et al. |
| 6,035,855 A | 3/2000 | Faries, Jr. et al. |
| 6,077,267 A | 6/2000 | Huene |
| 6,087,636 A | 7/2000 | Faries, Jr. et al. |
| 6,091,058 A | 7/2000 | Faries, Jr. et al. |
| 6,102,044 A | 8/2000 | Naidyhorski |
| D441,996 S | 5/2001 | Wright |
| 6,231,596 B1 | 5/2001 | Collins |
| 6,255,627 B1 | 7/2001 | Faries, Jr. et al. |
| 6,259,067 B1 | 7/2001 | Faries, Jr. et al. |
| D447,900 S | 9/2001 | Wright |
| 6,341,704 B1 | 1/2002 | Michel, Jr. |
| 6,371,121 B1 | 4/2002 | Faries, Jr. et al. |
| 6,448,571 B1 | 9/2002 | Goldstein |
| 6,586,950 B1 | 7/2003 | Sargent et al. |
| 6,593,552 B1 | 7/2003 | Li |
| 6,701,174 B1 | 3/2004 | Krause et al. |
| 6,810,881 B2 | 11/2004 | Faries, Jr. et al. |
| 6,860,271 B2 | 3/2005 | Faries, Jr. et al. |
| 6,884,970 B2 | 4/2005 | Lehman |
| 6,910,485 B2 | 6/2005 | Faries, Jr. et al. |
| 6,918,395 B2 | 7/2005 | Faries, Jr. et al. |
| 6,927,365 B2 | 8/2005 | Li |
| 7,041,941 B2 | 5/2006 | Faries, Jr. et al. |
| 7,128,275 B2 | 10/2006 | Kammer et al. |
| 7,176,030 B2 | 2/2007 | Faries, Jr. et al. |
| D546,943 S | 7/2007 | Kammer et al. |
| D546,944 S | 7/2007 | Kammer et al. |
| D547,444 S | 7/2007 | Kammer et al. |
| 7,276,675 B2 | 10/2007 | Faries, Jr. et al. |
| 7,307,245 B2 | 12/2007 | Faries, Jr. et al. |
| 7,309,472 B2 | 12/2007 | Michaelson et al. |
| 7,311,660 B2 | 12/2007 | Gomez |
| 7,347,210 B2 | 3/2008 | Faries, Jr. et al. |
| 7,350,373 B1 | 4/2008 | Faries, Jr. et al. |
| D568,989 S | 5/2008 | Kammer et al. |
| D569,970 S | 5/2008 | Kammer et al. |
| 7,417,205 B2 | 8/2008 | Faries, Jr. et al. |
| 7,418,966 B2 | 9/2008 | Faries, Jr. et al. |
| 7,441,714 B2 | 10/2008 | Kammer et al. |
| 7,459,657 B2 | 12/2008 | Kammer et al. |
| 7,560,667 B2 | 7/2009 | Kammer et al. |
| 7,671,302 B1 | 3/2010 | Faries, Jr. et al. |
| 7,728,262 B1 | 6/2010 | Faries, Jr. et al. |
| 7,811,522 B2 | 10/2010 | Mathus et al. |
| 7,854,230 B2 | 12/2010 | Faries, Jr. et al. |
| 7,854,387 B2 | 12/2010 | Kammer et al. |
| 7,874,167 B2 | 1/2011 | Kammer et al. |
| 7,903,957 B2 | 3/2011 | Kammer et al. |
| 7,959,860 B2 | 6/2011 | Faries, Jr. et al. |
| 8,148,666 B2 | 4/2012 | Faries, Jr. et al. |
| 8,148,667 B2 | 4/2012 | Faries, Jr. et al. |
| 8,153,937 B2 | 4/2012 | Faries et al. |
| 2003/0132216 A1 | 7/2003 | Li |
| 2003/0231990 A1 | 12/2003 | Faries, Jr. et al. |
| 2004/0200480 A1 | 10/2004 | Faries, Jr. et al. |
| 2004/0200483 A1 | 10/2004 | Faries, Jr. et al. |
| 2004/0208780 A1 | 10/2004 | Faries, Jr. et al. |
| 2004/0225265 A1 | 11/2004 | Tapadiya |
| 2005/0247169 A1 | 11/2005 | Faries, Jr. et al. |
| 2006/0065276 A1 | 3/2006 | Kammer et al. |
| 2006/0086361 A1 | 4/2006 | Kammer et al. |
| 2006/0091128 A1 | 5/2006 | Kammer et al. |
| 2006/0091129 A1 | 5/2006 | Colonna |
| 2006/0194324 A1 | 8/2006 | Faries, Jr. et al. |
| 2006/0260443 A1 | 11/2006 | Faries, Jr. et al. |
| 2006/0271017 A1 | 11/2006 | Booth et al. |
| 2006/0289016 A1 | 12/2006 | Kammer et al. |
| 2006/0289445 A1 | 12/2006 | Colonna |
| 2007/0084936 A1 | 4/2007 | Kammer et al. |
| 2007/0089753 A1 | 4/2007 | Faries, Jr. et al. |
| 2008/0152937 A1 | 6/2008 | Kammer et al. |
| 2008/0272199 A1 | 11/2008 | Kammer et al. |
| 2009/0014547 A1 | 1/2009 | Kammer et al. |
| 2009/0061053 A1 | 3/2009 | Gaylor et al. |
| 2009/0112057 A1 | 4/2009 | Kammer et al. |
| 2009/0255540 A1 | 10/2009 | Faries, Jr. |
| 2009/0301107 A1 | 12/2009 | Kammer et al. |
| 2010/0116810 A1 | 5/2010 | Faries, Jr. et al. |
| 2010/0200561 A1 | 8/2010 | Faries, Jr. et al. |

(56) References Cited

U.S. PATENT DOCUMENTS

2011/0270367 A1 11/2011 Faries, Jr. et al.
2012/0053518 A1 3/2012 Faries, Jr. et al.
2012/0187104 A1 7/2012 Heymann et al.

OTHER PUBLICATIONS

PCT International Preliminary Report on Patentability and Written Opinion, (8 pages), Oct. 12, 2010.

* cited by examiner

METHOD AND APPARATUS FOR WARMING MEDICAL SOLUTIONS IN A THERMAL TREATMENT SYSTEM EMPLOYING A REMOVABLE BASIN

CROSS-REFERENCE TO RELATED APPLICATIONS

This application claims priority from U.S. Provisional Patent Application Ser. No. 61/043,415, entitled "Method and Apparatus For Warming Medical Solutions in a Thermal Treatment System Employing a Removable Basin" and filed Apr. 9, 2008, the disclosure of which is incorporated herein by reference in its entirety.

BACKGROUND OF THE INVENTION

1. Technical Field

The present invention embodiments pertain to surgical drapes and corresponding devices for use with thermal treatment systems to enable thermal treatment of a medical solution. In particular, the present invention embodiments enable utilization of a surgical drape in a thermal treatment system such as is described in U.S. Pat. No. 7,128,275, where the system includes a removable or disposable basin to thermally treat medical solutions.

2. Discussion of Related Art

U.S. Pat. No. 7,128,275 to Kammer et al. describes a liquid warming device that heats sterile fluids and includes a removable basin to receive fluids to be warmed by the device. When the removable basin is placed within a receptacle of the device, a limit switch is engaged by the basin to activate a heater. The activated heater applies heat to the receptacle that is transferred to the basin and fluids disposed within the basin. The liquid warming device of Kammer et al. further includes a surgical drape that is connected to an upper rim and/or an outside wall of the basin such that the basin extends down through a hole in the surgical drape. While the surgical drape extends around portions of the liquid warming device, the basin is not covered by the drape but rather comes in direct contact with liquid and/or other items that are placed within the basin for thermal treatment.

In many applications in which the liquid warming device of Kammer et al. is utilized, (e.g., surgical applications), a sterile boundary or field must be maintained between the fluids and/or other items being warmed by the device and any portion of the device with which such items are in contact. Since the fluids and/or other items are applied directly within the removable basin, at least the surface portions which contact the items must be sterilized prior to use of the device. This typically requires removing the basin from the device and re-sterilization of the basin after each use or, alternatively, providing another sterilized basin to replace the used basin after each use of the device. This can become costly to either re-sterilize a basin after each use or provide new, sterilized basin each time the device is to be used.

OBJECTS AND SUMMARY OF THE INVENTION

Accordingly, it is an object of the present invention to provide a sterile barrier for a thermal treatment system that typically employs a removable basin to activate the heater of the thermal treatment system, where the sterile barrier is easy to install and use with the thermal treatment system.

It is another object of the present invention to provide a sterile barrier for such a thermal treatment system that is easy to manufacture and economically viable to be limited to a single use with the thermal treatment system.

Yet another object of the present invention is to provide a sterile barrier for such thermal treatment system that is reliable in maintaining the sterile barrier during use of the system.

A further object of the present invention is to provide a sterile barrier that facilitates use of the thermal treatment system without the requirement of the removable basin.

Still another object of the present invention is to provide a sterile barrier that can be used with the removable basin of such thermal treatment system such that it is not necessary to maintain sterility of the removable basin (i.e., the basin need not be sterilized and/or replaced after each use of the thermal treatment system).

The aforesaid objects may be achieved individually and/or in combination, and it is not intended that the present invention be construed as requiring two or more of the objects to be combined unless expressly required by the claims attached hereto.

According to the present invention, a drape device is provided for use with a thermal treatment system, where the thermal treatment system comprises a receptacle dimensioned to receive a basin, a heater to heat items placed within the receptacle and a limit switch that is operable to identify when the basin or other item is placed within the receptacle and to further activate the heater upon identification by the limit switch of the basin or other item being placed within the receptacle. The drape device drape comprises a drape including a flexible material that conforms to at least a portion of the receptacle upon being placed within the receptacle of the thermal treatment system, where the drape is further configured to receive and retain fluids and other items within the receptacle and to provide a barrier between items placed on the drape and the receptacle. The drape device further comprises engaging structure configured to engage the drape and one of the basin and the receptacle so as to facilitate operation of the limit switch and activation of the heater when the drape device is connected with the thermal treatment system and at least one item is placed on the drape within the receptacle.

In one embodiment, the engaging structure includes an actuation member that facilitates operation of the limit switch and activation of the heater without the use of the basin.

In another embodiment, the engaging structure is securable to the basin to facilitate securing of the drape within the basin during use of the thermal treatment system.

The above and still further features and advantages of the present invention will become apparent upon consideration of the following detailed description of specific embodiments thereof, particularly when taken in conjunction with the accompanying drawings wherein like reference numerals in the various figures are utilized to designate like components.

DETAILED DESCRIPTION OF THE PREFERRED EMBODIMENTS

Figure 1:
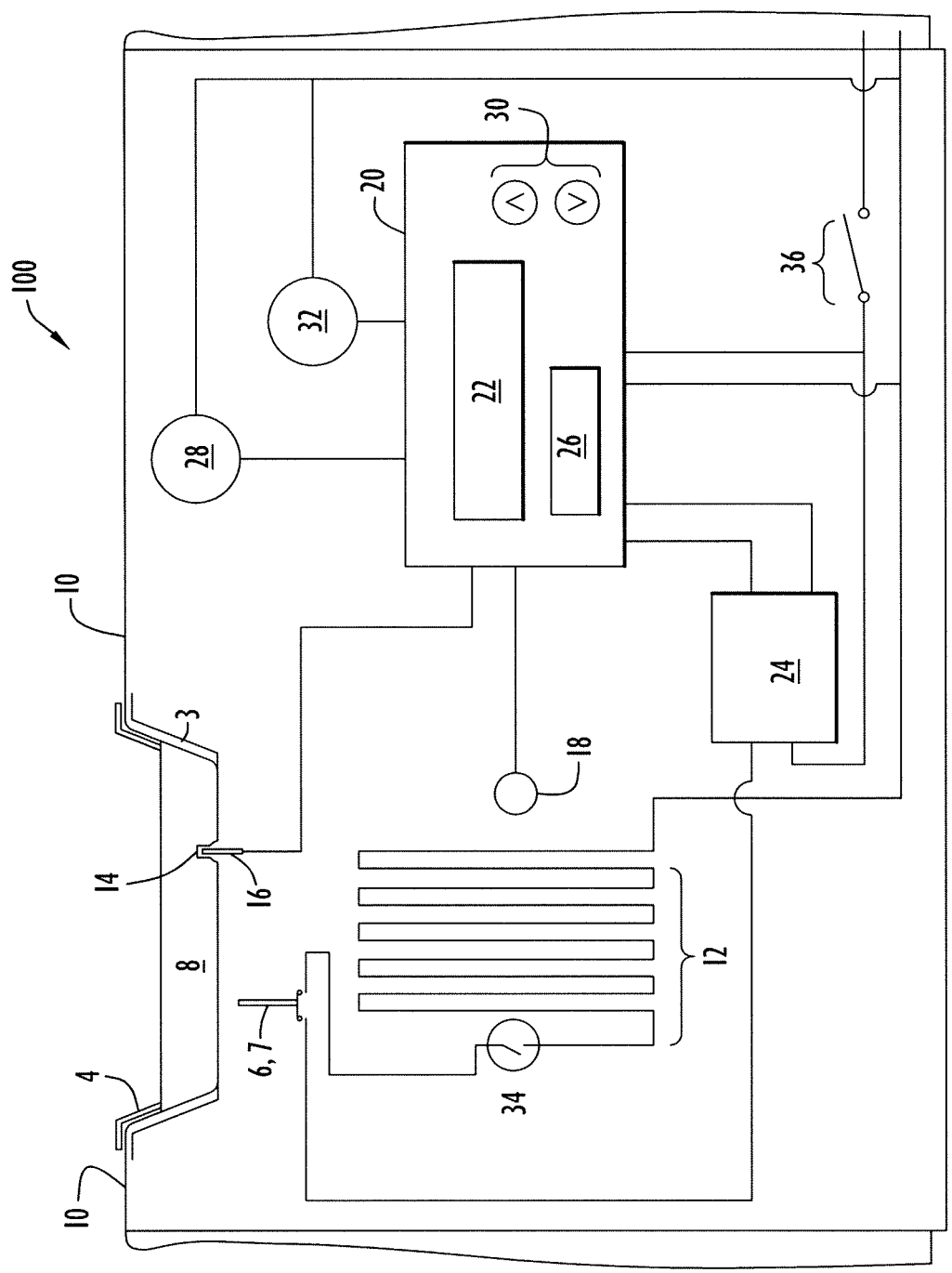
FIG. 1 is a schematic diagram of an exemplary thermal treatment system that may be employed by an embodiment of the present invention.

An exemplary thermal treatment system that may be employed by the present invention embodiments is illustrated in FIG. 1. Initially, the thermal treatment system may be of the type disclosed in U.S. Pat. No. 7,128,275 (Kammer et al.), the disclosure of which is incorporated herein by reference in its entirety. Specifically, fluid warming system 100 includes a warming receptacle 3, a removable or disposable basin 4 within receptacle 3, a limit switch 6, 7, a heater 12 and a fluid temperature controller 20. Sterile fluid 8 is placed within removable basin 4, where the basin includes an integral thermocouple well 14 to receive a temperature sensor or thermocouple 16 that protrudes into the receptacle 3 (e.g., at a bottom wall location of the receptacle 3 as can be seen in FIG. 1). Heater 12 selectively applies heat to receptacle 3 that is transferred to basin 4 and fluid 8. The fluid warming system further includes a main power or on/off switch 36, and may include a mechanical thermostat 34 (e.g., a bimetallic thermostat) to provide secondary protection against a failed control system. The mechanical thermostat acts as a switch to disable the heater when the heater temperature exceeds a set temperature.

A modified surgical drape 10 is connected to the upper rim of basin 4 and/or the basin outside wall, where the basin extends down through a hole in the surgical drape. The interaction between drape 10 and basin 4 may be implemented by a simple interference fit, where the basin is inserted into the drape hole and stretches the drape to facilitate attachment of the drape to the basin sufficiently to maintain the sterile field. Alternatively, the drape may be bonded to the basin outer wall or to the underside of the basin rim.

Indicator lamps 28, 32 are visible through the drape and are viewable from a distance to indicate the fluid temperature status. Indicator lamp 28 conveys an indication of the fluid temperature attaining a target temperature, or a temperature within a certain tolerance of that target temperature. In contrast, indicator lamp 32 indicates the presence of power to the fluid warming system (e.g., closure of main on/off switch 36) and a fluid temperature not within a certain tolerance of the target temperature. Indicator lamp 32 is typically not illuminated unless limit switch 6, 7 indicates that a basin is present as discussed below.

Fluid temperature sensor or thermocouple 16 is placed in thermal contact with thermocouple well 14 and in electrical contact with fluid temperature controller 20. In order to isolate the fluid temperature controller from current used in heater 12, a solid state relay 24 is used to translate control signals from the fluid temperature controller to effectively close a switch and provide current to the heater. Controller 20 varies the set point for the temperature of heater 12 which is measured by a heater temperature detector 18. A user may alter a target temperature 26 for the fluid through the use of input keys 30. The target temperature and the current temperature of the fluid may be displayed on a display 22. A maximum temperature is used as the set point temperature for the heater until the sterile fluid is relatively close to the target temperature. As the temperature of the sterile fluid approaches the target temperature, the set point for the heater is reduced thus slowing the rate of temperature increase of the sterile fluid.

Figure 2:
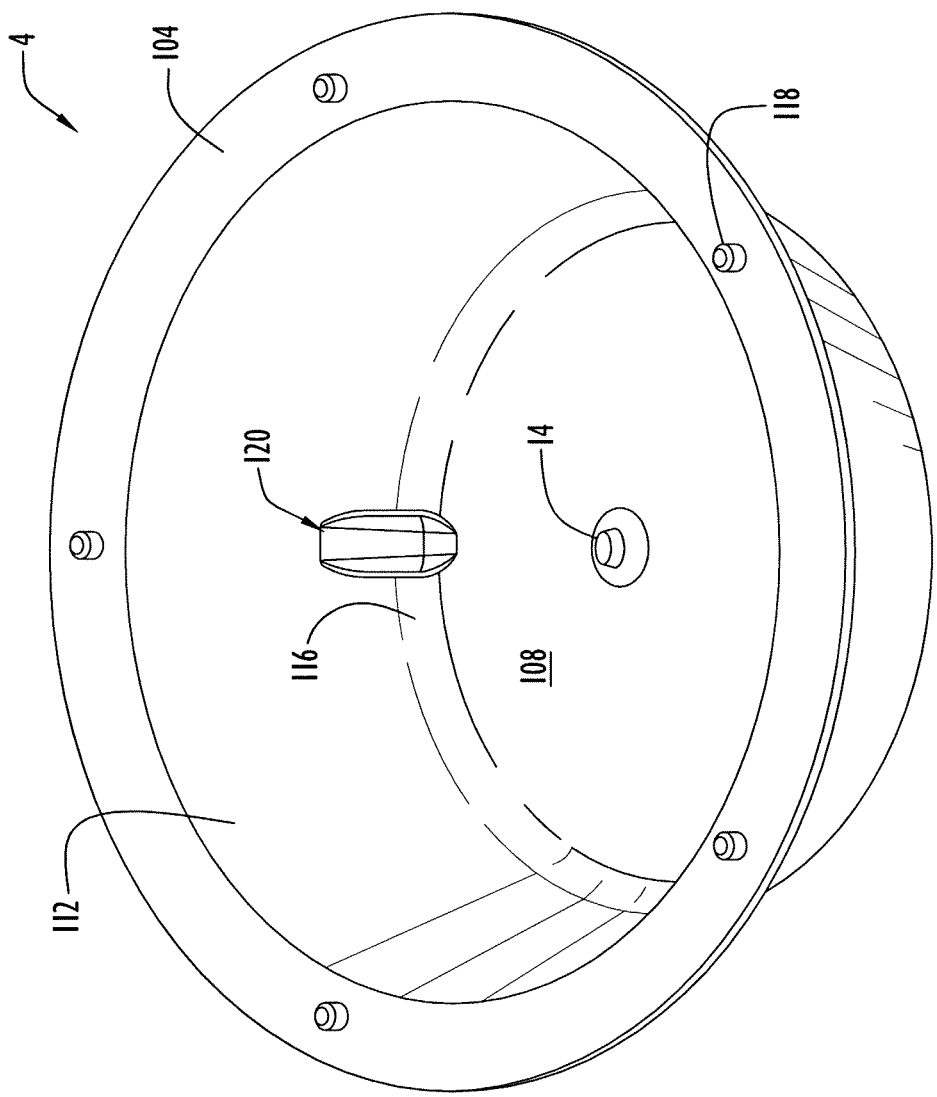
FIG. 2 is a view in perspective of a removable basin of the system of FIG. 1.

An exemplary basin 4 for fluid warming system 100 is illustrated in FIG. 2. Specifically, basin 4 includes a rim 104 with a series of substantially cylindrical posts or nubs 118 disposed thereon, a bottom wall 108, a side wall 112, and a sloped ring 116 disposed between the bottom and side walls. Thermocouple well 14 is defined in basin bottom wall 108, while an alignment channel 120 is present at the intersection of bottom wall 108 and a portion of side wall 112. In particular, thermocouple well 14 includes an interior protruding bottom wall surface portion of the basin 4 that defines the cavity or well on the outer bottom wall surface portion which receives thermocouple 16. The alignment channel fits over a corresponding ridge in the fluid warming system to provide an aid in aligning the basin relative to the fluid warming system. This enables thermocouple 16 to be forced into an interference fit in thermocouple well 14.

Figure 3:
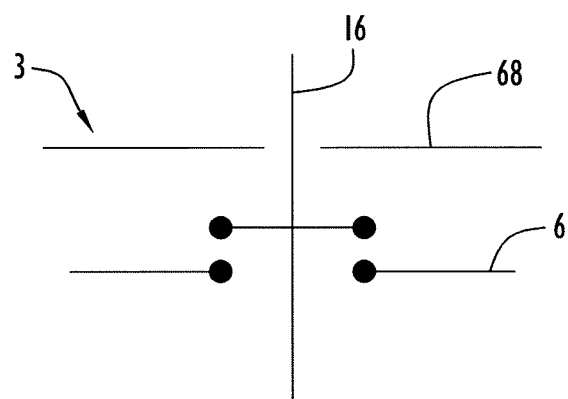
FIGS. 3-4 are schematic illustrations of a limit switch employed by the system of FIG. 1.
Figure 4:
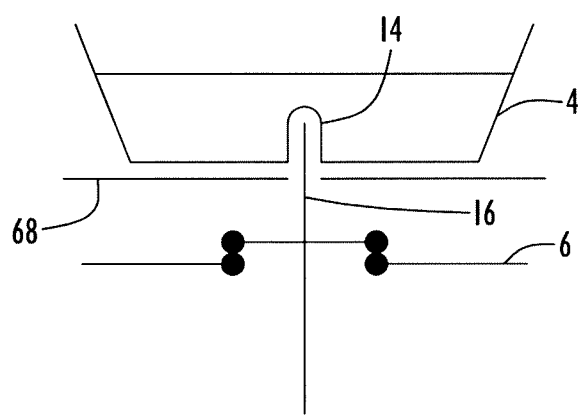

Basin limit switch 6, 7 (FIG. 1) prevents power from reaching heater 12 unless appropriate conditions exist to allow enablement of the heater. The basin limit switch basically detects the absence of a removable basin and the use of a basin without a corresponding well. Referring to FIGS. 3-4, heater 12 includes or is coupled to a heater plate or conductive material 68 providing heat from heater 12 to receptacle 3. Thermocouple or temperature sensor 16 protrudes through heater plate 68 and into receptacle 3. The temperature sensor 16 is further coupled to limit switch 6. When basin 4 is appropriately placed in receptacle 3 (FIG. 4), thermocouple well 14 is aligned with and receives thermocouple 16. The thermocouple is displaced sufficiently by thermocouple well 14 to close basin limit switch 6 and enable heater 12 to heat receptacle 3.

Figure 5A:
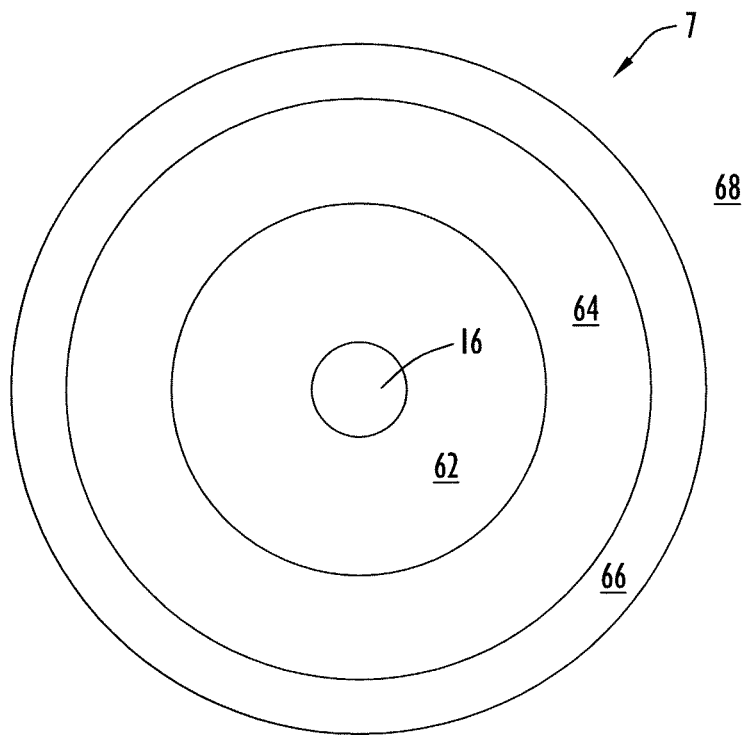
FIG. 5A is a top view in plan of an alternative limit switch that may be employed by the system of FIG. 1.
Figure 5B:
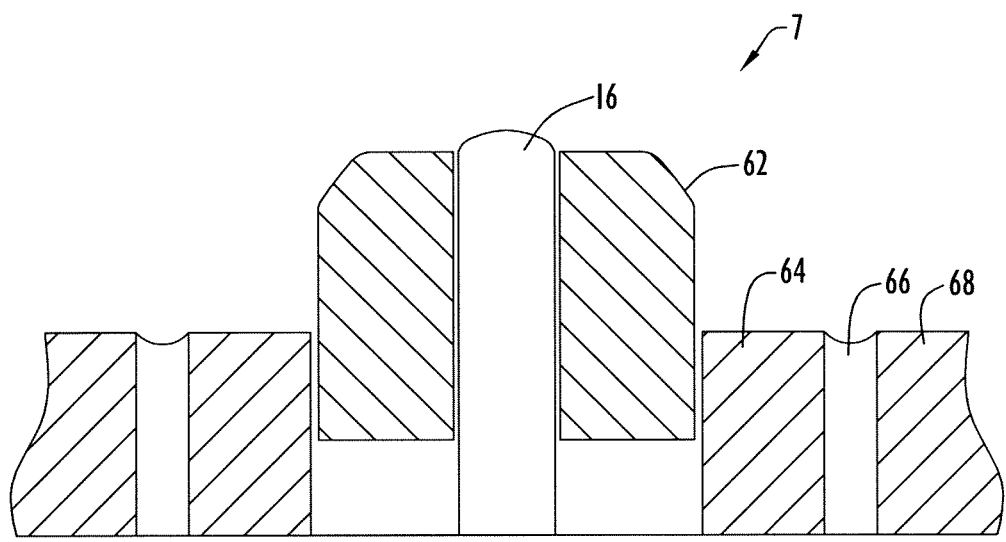
FIG. 5B is a view in elevation and partial section of the limit switch of FIG. 5A.

An embodiment of limit switch 7 is illustrated in FIGS. 5A-5B. Specifically, limit switch 7 includes thermocouple 16 surrounded by a limit switch actuator 62, a limit switch guide 64, an insulating zone 66, and conductive material 68. The conductive material conveys heat from heater 12 disposed below conductive material 68 to the bottom of basin 4. Thermocouple 16 is substantially isolated from the temperature of conductive material 68 by limit switch guide 64 and insulating zone 66. When basin 4 is placed in receptacle 3 with thermocouple well 14 aligned with thermocouple 16, the basin pushes down on limit switch actuator 62. The limit switch actuator moves downward relative to thermocouple 16, limit switch guide 64, insulating zone 66, and conductive material 68 and activates limit switch 7 to indicate that an appropriate basin is in place and to enable heater 12 to heat receptacle 3.

Figure 6A:
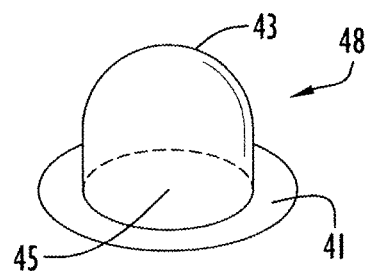
FIG. 6A is a view in perspective of an actuation member for the system of FIG. 1 employing the limit switch of FIG. 3 to actuate the limit switch and enable thermal treatment of a medical solution according to an embodiment of the present invention.
Figure 6B:
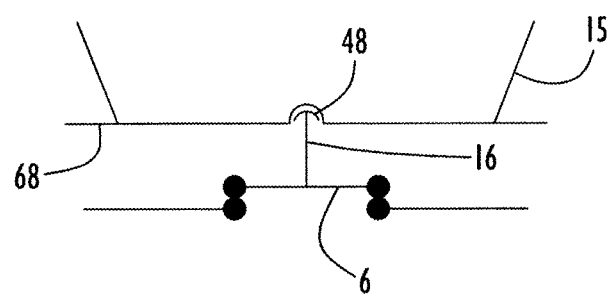
FIG. 6B is a schematic illustration of the interaction between the actuation member of FIG. 6A and the limit switch of FIG. 3 according to an embodiment of the present invention.

Fluid warming system 100 may further utilize surgical drape devices to contain the sterile fluid for warming. The surgical drape devices may be utilized with or without removable basin 4 as described below. In order to utilize a surgical drape device in fluid warming system 100 without basin 4 (and drape 10), limit switch 6, 7 needs to be actuated to enable heater 12 to heat receptacle 3. Accordingly, an actuation member 48 may be employed to actuate limit switch 6 (FIGS. 3-4) as illustrated in FIGS. 6A-6B. Specifically, actuation member 48 includes a base 41 and a cover member 43. Base 41 is generally annular and includes an opening 45 defined therethrough. Cover member 43 is generally semi-spherical and is attached to base 41 substantially coincident base opening 45. Cover member 43 is constructed of a suitably durable material (e.g., plastic, etc.) to prevent puncture by thermocouple 16. The actuation member may alternatively be implemented by the cover member (e.g., without base 41). The weight of the actuation member is sufficient to push down thermocouple 16 and activate limit switch 6 to enable heater 12 (FIG. 1) to heat sterile fluid contained by a drape in receptacle 3.

The actuation member is initially placed in receptacle 3 with base 41 disposed on heater plate 68 and the base opening and cover member substantially coincident the heater plate opening (FIG. 6B). Cover member 43 receives thermocouple 16 to actuate limit switch 6. In particular, the thermocouple distal end engages the upper end of cover member 43. The cover member upper end forces the thermocouple downward to actuate limit switch 6. The cover member may include sufficient weight and dimensions (e.g., less than the thermocouple protrusion) to displace thermocouple 16 in this manner, or the weight of the drape and/or sterile fluid within the drape container may provide the weight for the thermocouple displacement. In addition, the cover member is preferably configured and/or constructed with suitable materials (e.g., plastic, conducting, etc.) to enable a temperature measurement of the sterile fluid by the thermocouple through the cover member (and drape).

Once actuation member 48 is positioned to actuate limit switch 6, a drape 15 may be placed over the fluid warming system and within receptacle 3 (FIG. 1) to warm a sterile fluid in a drape container and provide a sterile field as described above. Specifically, sterile drape 15 (FIG. 6B) for use in fluid warming system 100 (without removable basin 4 and drape 10) is preferably transparent and typically disposed over the top and sides of fluid warming system 100 to provide a sterile field (similar to drape 10 as viewed in FIG. 1). A portion of drape 15 is disposed in heated receptacle 3 and serves as a sterile container or receptacle for sterile fluid to be heated and placed therein. Drape 15 is made from a material that is impervious to the sterile fluid and sufficiently soft and flexible to conform to receptacle walls. The thickness of the drape is preferably minimized to render thermal transfer therethrough most efficient, yet the thickness is sufficient to resist tearing and puncturing during normal use. The drape may be made of materials commonly used in hospitals for surgical drapes and has a thickness, by way of example only, of approximately 4.5 to 6.0 mils. However, the drape may have any desired thickness. Drape 15 may also be made of polyurethane film as disclosed for the drape in U.S. Pat. No. 4,934,152 (Templeton), the disclosure of which is incorporated herein by reference in its entirety. In addition, the drape may include sensors to detect the presence or absence of fluid within the receptacle and/or the presence of a drape leak. Examples of these types of drapes are disclosed in U.S. Pat. No. 6,810,881 (Faries, Jr. et al.), U.S. Pat. No. 6,910,485 (Faries, Jr. et al.) and U.S. Pat. No. 7,176,030 (Faries, Jr. et al.), the disclosures of which are incorporated herein by reference in their entireties. Since the actuation member is disposed outside the sterile field (e.g., beneath the drape), the actuation member need not be sterilized for each use.

Alternatively, the drape may be placed over the fluid warming system with actuation member 48 placed on the drape sterile surface (e.g., within the sterile field) substantially coincident limit switch 6 to actuate the limit switch through the drape in substantially the same manner described above. Since the actuation member is disposed within the sterile field (e.g., above the drape), the actuation member needs to be sterile for each use. Accordingly, the actuation member may be designed to be disposable after a single use and preferably provided presterilized and prepackaged in a manner to preserve its sterile state during storage. The actuation member may further be constructed of suitable materials (e.g., plastic, rubber, etc.) to enable sterilization prior to each use.

Figure 6C:
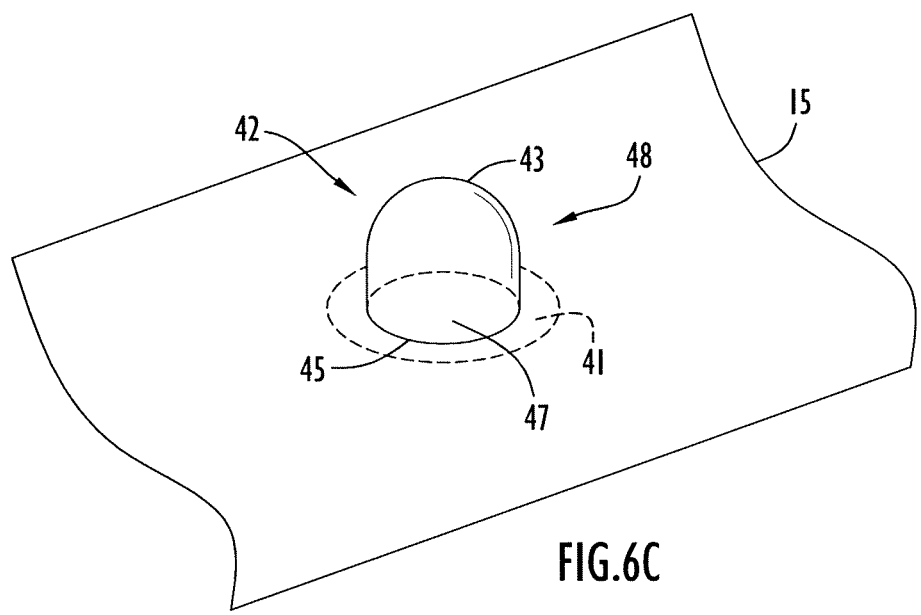
FIG. 6C is a view in perspective of a surgical drape for use with the system of FIG. 1 employing the limit switch of FIG. 3 according to an embodiment of the present invention.
Figure 6D:
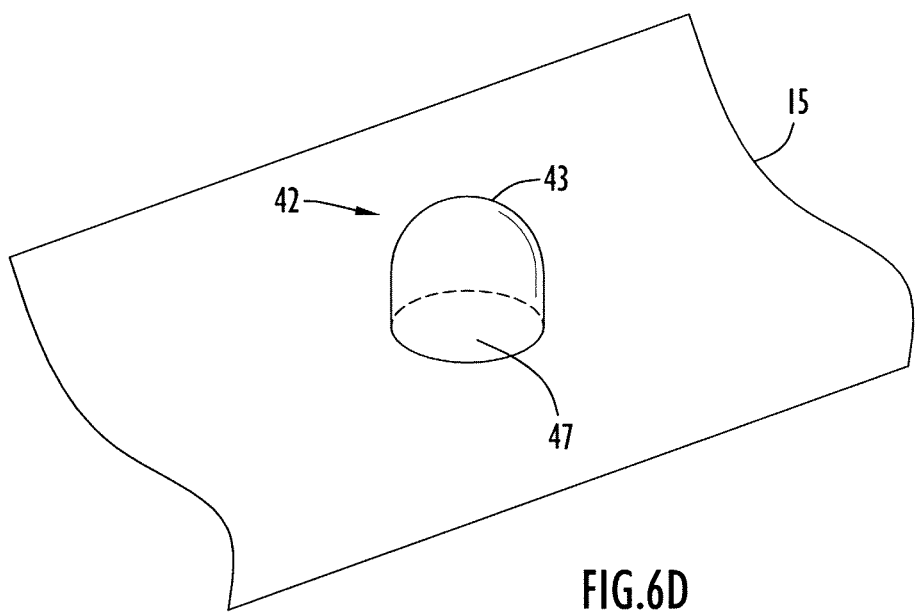
FIG. 6D is a view in perspective of another surgical drape for use with the system of FIG. 1 employing the limit switch of FIG. 3 according to an embodiment of the present invention.

Actuation member 48 may be attached to a drape according to an embodiment of the present invention to enable warming of a sterile fluid within fluid warming system 100 as illustrated in FIG. 6C. Specifically, drape 15 is substantially similar to the drape described above for FIG. 6B and includes a sensor receptacle 42 in the form of actuation member 48. The actuation member includes base 41 and cover member 43 each as described above. Base 41 is typically attached to the drape sterile surface, where drape 15 includes an opening 47 substantially coincident base opening 45. The actuation member may be attached or integrated into the drape by any conventional or other techniques (e.g., adhesion, heat welding, RF, etc.). The base is sealed to the drape to prevent leaks of sterile fluid from the drape container through the drape opening. Actuation member 48 may further be attached to the underside or non-sterile surface of drape 15, where the drape covers the actuation member (e.g., without the drape opening). Alternatively, base 41 may be attached to the drape non-sterile surface with cover member 41 extending through the drape opening beyond the drape sterile surface. In this case, the drape is sealed about the sensor receptacle to prevent leaks of sterile fluid from the drape container through the drape opening. In addition, drape 15 may include actuation member 48 without base 41, where cover member 43 is attached to the drape sterile (and/or non sterile) surface substantially coincident (and/or through) drape opening 47 as illustrated in FIG. 6D. The drape is sealed about the cover member to prevent leaks of sterile fluid from the drape container through the drape opening. Cover member 43 is configured to receive and sufficiently displace thermocouple 16 downward to actuate limit switch 6 as described below. The sensor receptacle protects the drape from puncture by thermocouple 16, and may further serve to indicate the orientation or alignment of the drape over the fluid warming system.

Figure 6E:
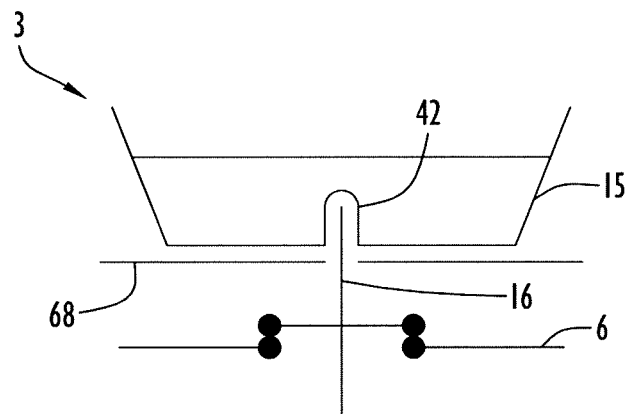
FIG. 6E is a schematic illustration of the interaction between the surgical drapes of FIGS. 6C-6D and the limit switch of FIG. 3 according to an embodiment of the present invention.

Operation of drape 15 with sensor receptacle 42 is described with reference to FIG. 6E. Specifically, drape 15 is typically positioned over fluid warming system 100 with a portion of the drape including sensor receptacle 42 disposed in receptacle 3 to form a drape container. The drape forms a sterile field above the receptacle to maintain sterility of a sterile medium or fluid placed in the drape container. Sensor receptacle 42 is positioned substantially coincident thermocouple 16 protruding through heater plate 68 to receive the thermocouple therein. Sensor receptacle 42 is configured to receive and sufficiently displace thermocouple 16 downward to actuate limit switch 6 to enable heating. In particular, the thermocouple distal end engages the upper end of sensor receptacle 42 (e.g., the cover member top surface) upon insertion into the sensor receptacle. The sensor receptacle upper end forces the thermocouple downward to actuate limit switch 6. The cover member may include sufficient weight and dimensions to displace thermocouple 16 in this manner, or the weight of the sterile fluid within the drape container may provide the weight for the thermocouple displacement as described above. In addition, the cover member is preferably configured and/or constructed with suitable materials (e.g., plastic, conducting, etc.) to enable a temperature measurement of the sterile fluid by the thermocouple when inserted within sensor receptacle 42.

Figure 6F:
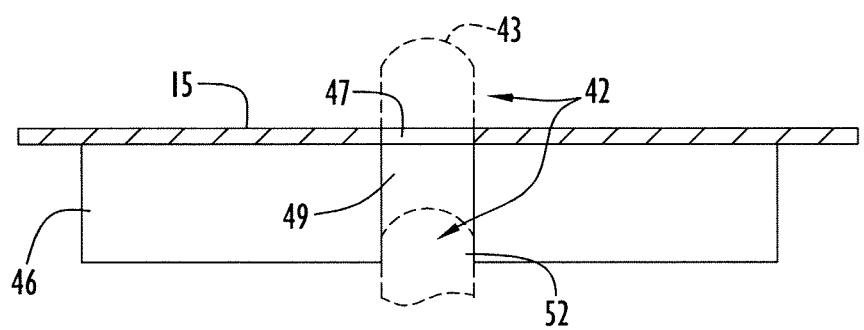
FIG. 6F is a view in elevation and partial section of a surgical drape including a plate for use with the system of FIG. 1 employing the limit switch of FIG. 3 according to an embodiment of the present invention.

A plate may be secured to the drape non-sterile surface to provide sensor receptacle 42 according to an embodiment of the present invention as illustrated in FIG. 6F. Specifically, drape 15 is substantially similar to the drape described above for FIG. 6B and includes a plate 46 attached to the underside or non-sterile surface the drape. The plate may be attached or integrated into the drape by any conventional or other techniques (e.g., adhesion, heat welding, RF, etc.). The plate is generally circular and may include sensor receptacle 42 in the form of a channel 52 defined in the plate. The channel (and/or plate thickness) includes dimensions sufficient to receive and displace thermocouple 16 downward to actuate limit switch 6.

Alternatively, sensor receptacle 42 may include cover member 43 described above and attached to the plate and/or drape sterile surface. The actuation member may be attached or integrated into the plate and/or drape by any conventional or other techniques (e.g., adhesion, heat welding, RF, etc.). In this case, plate 46 includes an opening 49 defined therethrough and aligned with drape opening 47. Cover member 43 is attached to the plate and/or drape sterile surface substantially coincident drape and plate openings 47, 49. Cover member 43 receives thermocouple 16 through the plate and drape openings and includes dimensions sufficient to displace the thermocouple downward to actuate limit switch 6 as described below. The cover member may alternatively be attached to the plate substantially coincident opening 49 with the drape (without opening 47) covering the sensor receptacle. The plate and/or sensor receptacle protect the drape from puncture by thermocouple 16, and may further serve to indicate the orientation or alignment of the drape over the fluid warming system.

Figure 6G:
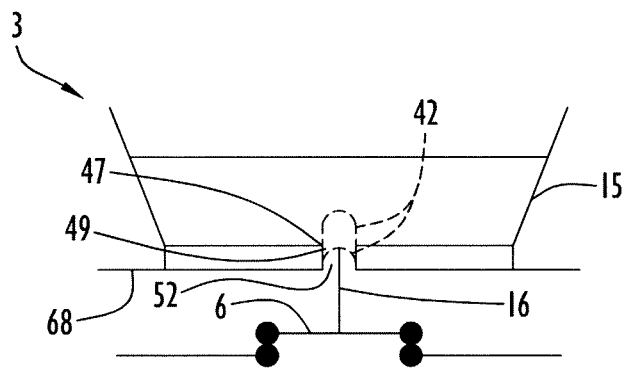
FIG. 6G is a schematic illustration of the interaction between the surgical drape of FIG. 6F and the limit switch of FIG. 3 according to an embodiment of the present invention.

Operation of drape 15 with plate 46 is described with reference to FIG. 6G. Specifically, drape 15 is typically positioned over fluid warming system 100 with a portion of the drape including sensor receptacle 42 (and plate 46) disposed in receptacle 3 to form a drape container. The drape forms a sterile field above the receptacle to maintain sterility of a sterile medium or liquid placed in the drape container. Sensor receptacle 42 is positioned substantially coincident thermocouple 16 protruding through heater plate 68 to receive the thermocouple therein. Sensor receptacle 42 is configured to receive and sufficiently displace thermocouple 16 downward to actuate limit switch 6 to enable heating. In particular, the thermocouple distal end engages the upper end of sensor receptacle 42 (e.g., the cover member or plate channel top surface) upon insertion into the sensor receptacle. The sensor receptacle upper end forces the thermocouple downward to actuate limit switch 6. The cover member and/or plate may include sufficient weight and dimensions to displace thermocouple 16 in this manner, or the weight of the sterile fluid within the drape container may provide the weight for the thermocouple displacement. In addition, the plate and cover member are preferably configured and/or constructed with suitable materials (e.g., plastic, conducting, etc.) to enable a temperature measurement of the sterile fluid by the thermocouple when inserted within sensor receptacle 42.

Drapes 15 described above may further include a preformed container portion contoured to match the contour of the receptacle. The preformed container portion is typically thicker than the remaining portions of the drape described above in order to resist puncture and enable the container portion to maintain the shape of the receptacle. By way of example only, the container portion may be made of a heavy gauge polyethylene/ionomer resin blend having a thickness of approximately ten to sixteen mils. The percentage of ionomer resin in the blend is in the approximate range of forty to seventy percent. In this case, the preformed container portion may include sensor receptacle 42 (and/or plate 46) in substantially the same manner described above. The drapes described above are designed to be disposable after a single use and are provided presterilized and prepackaged in a manner to preserve their sterile state during storage.

Figure 7A:
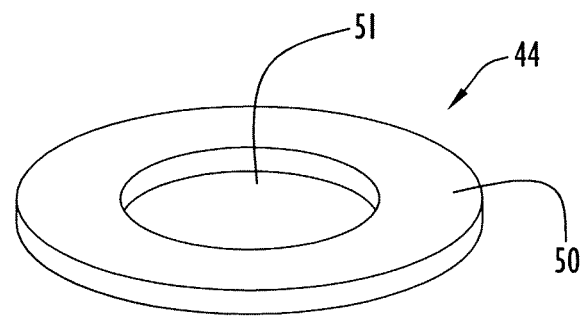
FIG. 7A is a view in perspective of an actuation member for use with the system of FIG. 1 employing the limit switch of FIG. 5B to actuate the limit switch and enable thermal treatment of a medical solution according to an embodiment of the present invention.
Figure 7B:
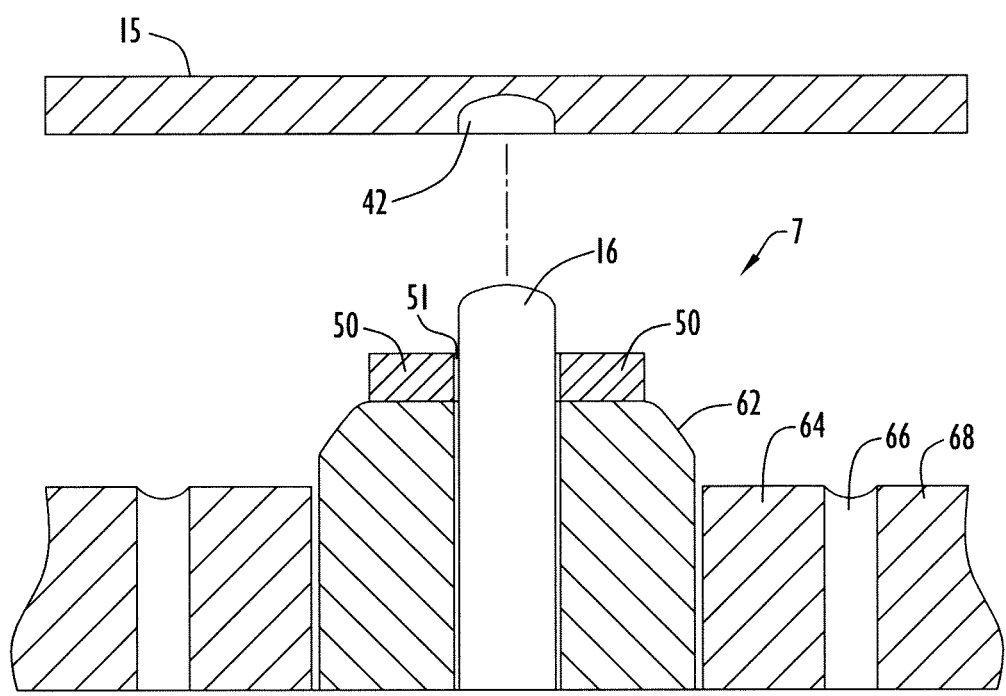
FIG. 7B is an exploded view in elevation and partial section of the actuation member of FIG. 7A and the limit switch of FIG. 5B according to a present invention embodiment.

In order to enable a surgical drape to be utilized by the fluid warming system without basin 4 (and drape 10), an actuation member 44 may be employed to actuate limit switch 7 (FIGS. 5A-5B) as illustrated in FIGS. 7A-7B. Specifically, actuation member 44 includes a body 50 in the form of a generally annular ring with an opening 51 defined therethrough. The dimensions of the actuation member are sufficient to enable the actuation member body to rest on limit switch actuator 62, while receiving thermocouple 16 through opening 51. The weight of the actuation member body is sufficient to push down on limit switch actuator 62. The limit switch actuator moves downward relative to thermocouple 16, limit switch guide 64, insulating zone 66, and conductive material 68 and activates limit switch 7 to enable heater 12 (FIG. 1) to heat receptacle 3.

Once actuation member 44 is positioned to actuate limit switch 7, a drape 15 may be placed over the fluid warming system and within receptacle 3 (FIG. 1) to warm a sterile fluid in a drape container and provide a sterile field as described above. The drape may be implemented by drapes 15 (e.g., FIGS. 6B-6D) described above. In the case of drape 15 employing sensor receptacle 42, the sensor receptacle may be configured simply to receive the thermocouple therein to enable a temperature measurement (e.g., without being configured to displace the thermocouple). Since the actuation member is disposed outside the sterile field (e.g., beneath the drape), the actuation member need not be sterilized for each use.

Alternatively, the drape may be placed over the fluid warming system with actuation member 44 placed on the drape sterile surface (e.g., within the sterile field) substantially coincident limit switch 7 to actuate the limit switch through the drape in substantially the same manner described above. In the case of drape 15 employing sensor receptacle 42 (FIGS. 6C-6D), the sensor receptacle is preferably configured to enable actuation member 44 to be placed on the drape sterile surface with cover member 43 inserted through actuation member opening 51. Since the actuation member is disposed within the sterile field (e.g., above the drape), the actuation member needs to be sterile for each use. Accordingly, the actuation member may be designed to be disposable after a single use and preferably provided presterilized and prepackaged in a manner to preserve its sterile state during storage. The actuation member may further be constructed of suitable materials (e.g., plastic, rubber, etc.) to enable sterilization prior to each use.

Figure 7C:
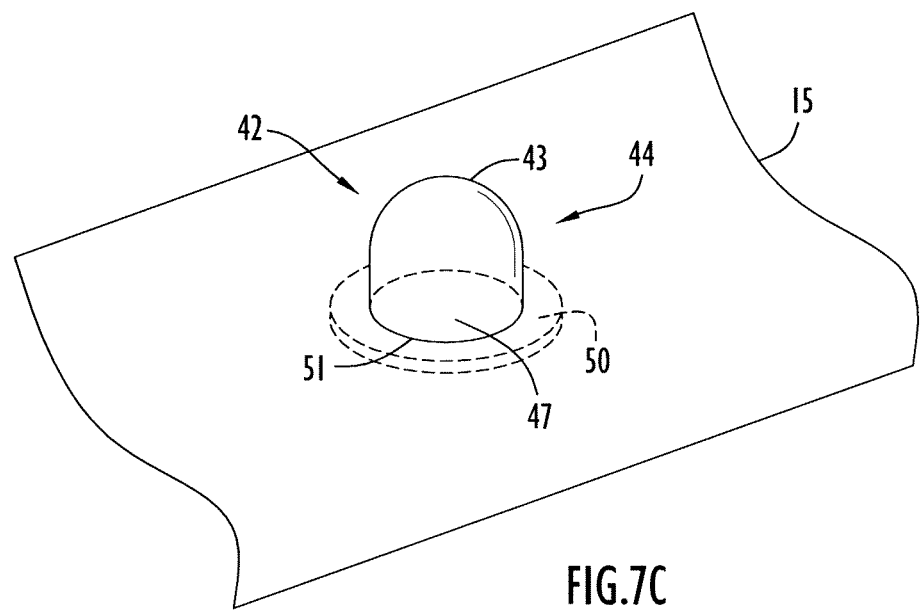
FIG. 7C is a view in perspective of a surgical drape including the actuation member of FIG. 7A according to an embodiment of the present invention.
Figure 7D:
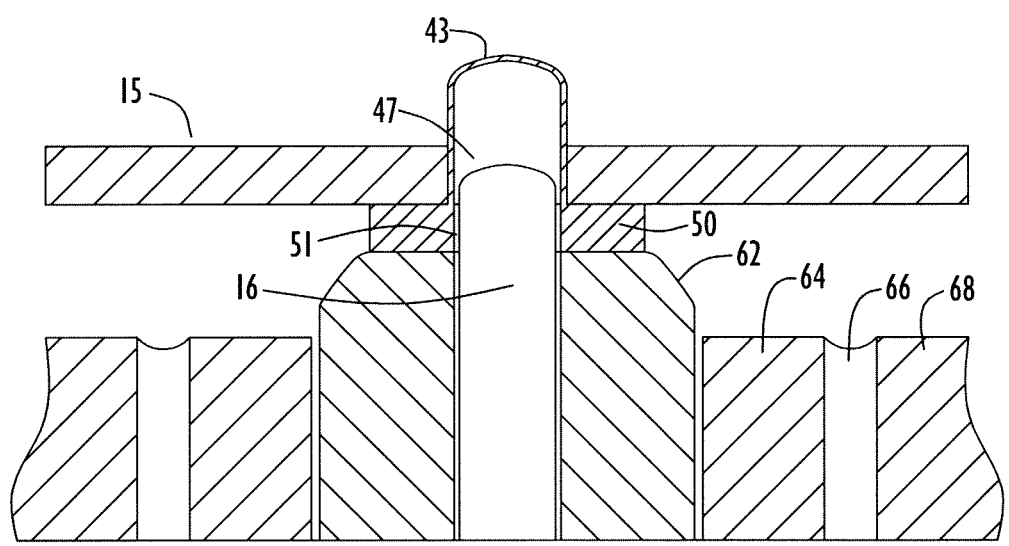
FIG. 7D is a view in elevation and partial section of the surgical drape of FIG. 7C and the limit switch of FIG. 5B according to an embodiment of the present invention.

Actuation member 44 may be attached to drape 15 according to an embodiment of the present invention to enable warming of a sterile fluid within fluid warming system 100 as illustrated in FIGS. 7C-7D. Specifically, drape 15 is substantially similar to the drape described above for FIG. 6B and includes sensor receptacle 42. The sensor receptacle includes actuation member 44 and a cover member 43 each as described above. Actuation member 44 is typically attached to the drape non-sterile surface, where drape 15 includes opening 47 substantially coincident actuation member opening 51. The actuation member may be attached or integrated into the drape by any conventional or other techniques (e.g., adhesion, heat welding, RF, etc.). Cover member 43 is attached to actuation member 44 substantially coincident actuation member opening 51, and extends through drape opening 47 beyond the drape sterile surface. The drape is sealed about the sensor receptacle to prevent leaks of sterile fluid from the drape container through the drape opening. The sensor receptacle protects the drape from puncture by thermocouple 16, and may further serve to indicate the orientation or alignment of the drape over the fluid warming system.

In operation, drape 15 with actuation device 44 may be placed over the fluid warming system (FIG. 7D) and within receptacle 3 (FIG. 1) to warm a sterile fluid in a drape container. The actuation member is positioned with the actuation member body resting on limit switch actuator 62 and thermocouple 16 extending through opening 51 and into cover member 43. The weight of the actuation member body is sufficient to push down on limit switch actuator 62. The limit switch actuator moves downward relative to thermocouple 16, limit switch guide 64, insulating zone 66, and conductive material 68 and activates limit switch 7 to enable heater 12 (FIG. 1) to heat receptacle 3. Sensor receptacle 42 may further be attached to the underside or non-sterile surface of drape 15, where the drape covers the sensor receptacle (e.g., without the drape opening) to enable heating of the sterile fluid in substantially the same manner described above. Alternatively, sensor receptacle 42 may be disposed on the drape sterile surface with cover member 43 substantially aligned with openings 47, 51 to enable heating of the sterile fluid in substantially the same manner described above.

Figure 7E:
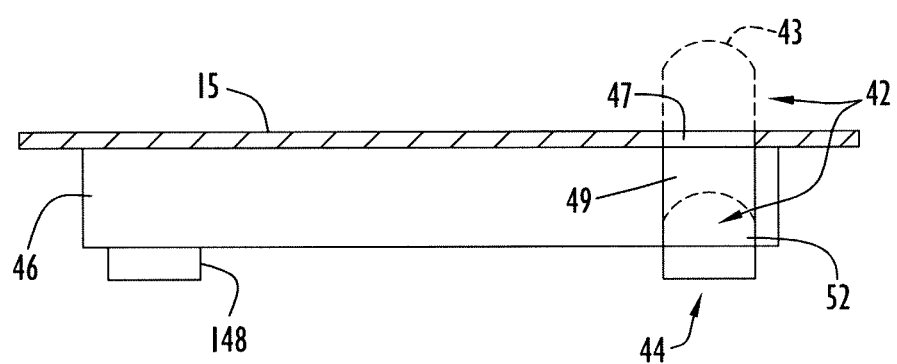
FIG. 7E is a view in elevation and partial section of a surgical drape including a plate and the member of FIG. 7A attached to the plate according to a present invention embodiment.
Figure 7F:
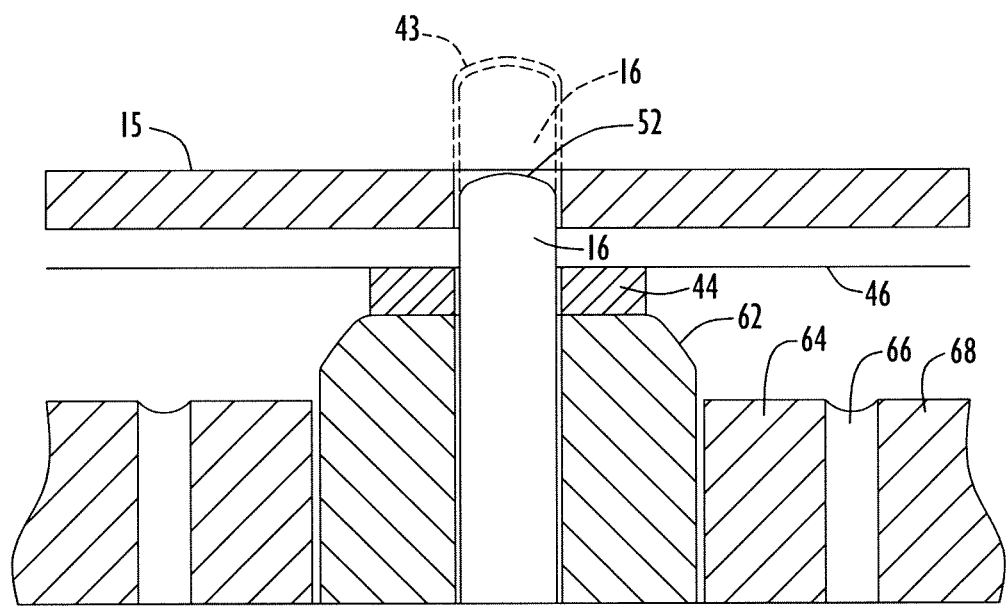
FIG. 7F is a view in elevation and partial section of the surgical drape of FIG. 7E and the limit switch of FIG. 5B according to an embodiment of the present invention.

A plate including actuation member 44 may be secured to the drape non-sterile surface to enable use of the drape by the fluid warming system without basin 4 (and drape 10) according to an embodiment of the present invention as illustrated in FIGS. 7E-7F. Specifically, drape 15 is substantially similar to the drape described above for FIG. 6B and includes plate 46 attached to the underside or non-sterile surface of drape 15. The plate may be attached or integrated into the drape by any conventional or other techniques (e.g., adhesion, heat welding, RF, etc.). The plate is generally circular and may include sensor receptacle 42 disposed toward a plate edge. Sensor receptacle 42 may include actuation member 44 as described above and a channel or opening 52 defined in the plate. The channel includes a closed upper end and extends from the plate bottom surface. Actuation member 44 is disposed on the underside of the plate with actuation member opening 51 substantially aligned with channel 52. The actuation member may be attached or integrated into the plate by any conventional or other techniques (e.g., adhesion, heat welding, RF, etc.). The channel (and/or plate thickness) includes dimensions sufficient to receive thermocouple 16 therein.

The sensor receptacle may further include actuation member 44 and a cover member 43 each as described above. Plate 46 includes opening 49 defined therethrough and aligned with a drape opening 47. Actuation member 44 is disposed on the underside of the plate with actuation member opening 51 substantially aligned with drape and plate openings 47, 49. Cover member 43 is attached to the plate and/or drape sterile surface substantially coincident openings 47, 49, 51 and receives thermocouple 16 through openings 47, 49, 51. The drape is sealed about the sensor receptacle to prevent leaks of sterile fluid from the drape container through the drape opening. The actuation member and/or sensor receptacle protects the drape from puncture by thermocouple 16, and may further serve to indicate the orientation or alignment of the drape over the fluid warming system.

Since the actuation member is secured to the underside of plate 46, the plate portion including the actuation member may be slightly elevated. This may result in the plate being oriented in a tilted fashion when disposed in heated receptacle 3 (FIG. 1). Accordingly, plate 46 may further include a foot 148 disposed toward an opposing plate edge relative to actuation member 44 to support plate 46 within receptacle 3. Foot 148 engages the receptacle bottom surface and includes dimensions suitable to support and maintain plate 46 in a substantially level orientation. The foot may be attached or integrated into the plate by any conventional or other techniques (e.g., adhesion, heat welding, RF, etc.).

In operation, drape 15 with plate 46 and actuation member 44 may be placed over the fluid warming system (FIG. 7F) and within receptacle 3 (FIG. 1) to warm a sterile fluid in a drape container. The plate is positioned with the actuation member body resting on limit switch actuator 62 and foot 148 engaging the receptacle bottom. Thermocouple 16 extends through opening 51 and into channel 49. In the case of the drape including a cover member, thermocouple 16 extends through openings 47, 49, 51 and into cover member 43. The weight of the actuation member body is sufficient to push down on limit switch actuator 62. The limit switch actuator moves downward relative to thermocouple 16, limit switch guide 64, insulating zone 66, and conductive material 68 and activates limit switch 7 to enable heater 12 (FIG. 1) to heat receptacle 3. Plate 46 may alternatively be attached to the drape sterile surface with channel 52, opening 49 and/or cover member 43 substantially aligned with drape opening 47. The actuation member actuates limit switch 7 through the drape to enable heating of the sterile fluid in substantially the same manner described above.

Figure 7G:
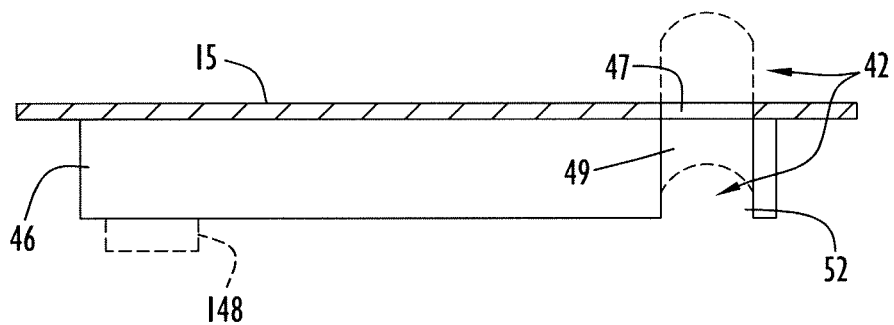
FIG. 7G is a view in elevation and partial section of a surgical drape including a plate serving to actuate the limit switch of FIG. 5B according to a present invention embodiment.
Figure 7H:
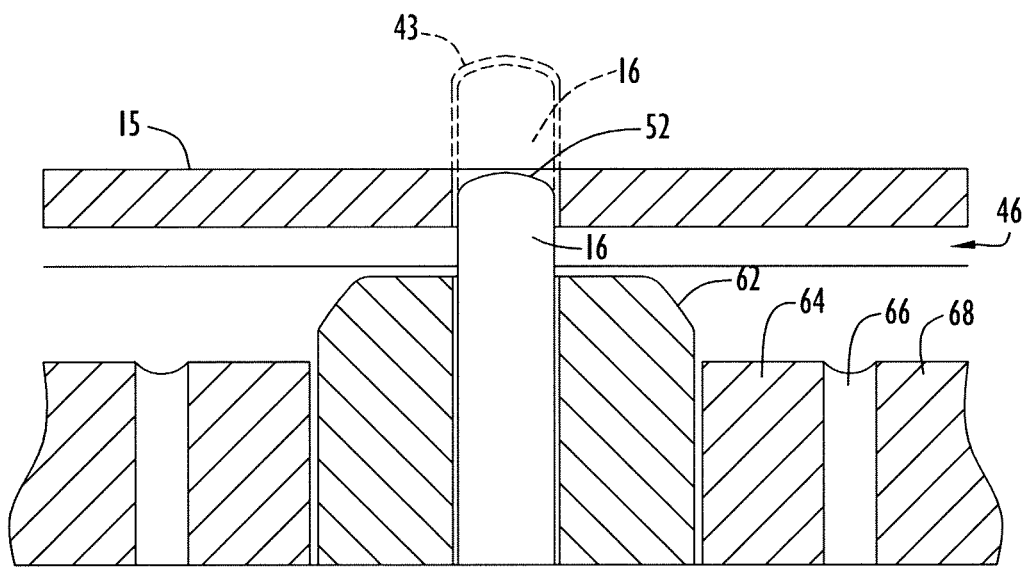
FIG. 7H is a view in elevation and partial section of the surgical drape of FIG. 7G and the limit switch of FIG. 5B according to an embodiment of the present invention.

A plate serving as an actuation device for limit switch 7 may be secured to the drape to enable use of the drape by the fluid warming system without basin 4 (and drape 10) according to an embodiment of the present invention as illustrated in FIGS. 7G-7H. Specifically, drape 15 is substantially similar to the drape described above for FIG. 7E and includes plate 46 preferably attached to the underside or non-sterile surface of drape 15. The plate may be attached or integrated into the drape by any conventional or other techniques (e.g., adhesion, heat welding, RF, etc.). The plate is generally circular and may include sensor receptacle 42 disposed toward a plate edge as described above. Sensor receptacle 42 may be in the form of a channel or opening 52 defined in the plate. The channel includes a closed upper end and extends from the plate bottom surface. The channel (and/or plate thickness) includes dimensions sufficient to receive thermocouple 16 therein.

The sensor receptacle may further include cover member 43 as described above. In this case, plate 46 includes opening or channel 49 defined therethrough and aligned 33 with a drape opening 47. Cover member 43 is attached to the plate and/or drape sterile surface substantially coincident openings 47, 49 and receives thermocouple 16 through those openings. The drape is sealed about the sensor receptacle to prevent leaks of sterile fluid from the drape container through the drape opening. Alternatively, the cover member may be attached to the plate with the drape covering the sensor receptacle. The plate and/or sensor receptacle protects the drape from puncture by thermocouple 16, and may further serve to indicate the orientation or alignment of the drape over the fluid warming system.

In operation, drape 15 with plate 46 may be placed over the fluid warming system (FIG. 7H) and within receptacle 3 (FIG. 1) to warm a sterile fluid in a drape container. The plate is positioned to receive thermocouple 16 within channel 52 and with the plate bottom surface portions proximate the channel resting on limit switch actuator 62. Thermocouple 16 extends into channel 52. In the case of the drape including a cover member, thermocouple 16 extends through openings 47, 49 and into cover member 43. The weight of the plate is sufficient to push down on limit switch actuator 62. The limit switch actuator moves downward relative to thermocouple 16, limit switch guide 64, insulating zone 66, and conductive material 68 and activates limit switch 7 to enable heater 12 (FIG. 1). Plate 46 may alternatively be disposed on the drape sterile surface with channel 52 and/or cover member 43 substantially aligned with drape opening 47. The plate actuates limit switch 7 through the drape to enable heating of the sterile fluid in substantially the same manner described above.

Since the plate portion engaging switch actuator 62 may be slightly elevated, the plate may be oriented in a tilted fashion when disposed in heated receptacle 3 (FIG. 1). Accordingly, plate 46 may further include foot 148 disposed toward an opposing plate edge relative to channel 52 to support plate 46 within receptacle 3. Foot 148 engages the receptacle bottom surface and includes dimensions suitable to support and maintain plate 46 in a substantially level orientation.

Drapes 15 described above (e.g., FIGS. 7B-7H) may further include a preformed container portion contoured to match the contour of the receptacle. The preformed container portion is typically thicker than the remaining portions of the drape in order to resist puncture and enable the container portion to maintain the shape of the receptacle. By way of example only, the container portion may be made of a heavy gauge polyethylene/ionomer resin blend having a thickness of approximately ten to sixteen mils. The percentage of ionomer resin in the blend is in the approximate range of forty to seventy percent. In this case, the preformed container portion may include sensor receptacle 42 (and/or plate 46) in substantially the same manner described above. The drapes described above are designed to be disposable after a single use and are provided presterilized and prepackaged in a manner to preserve their sterile state during storage.

Figure 8:
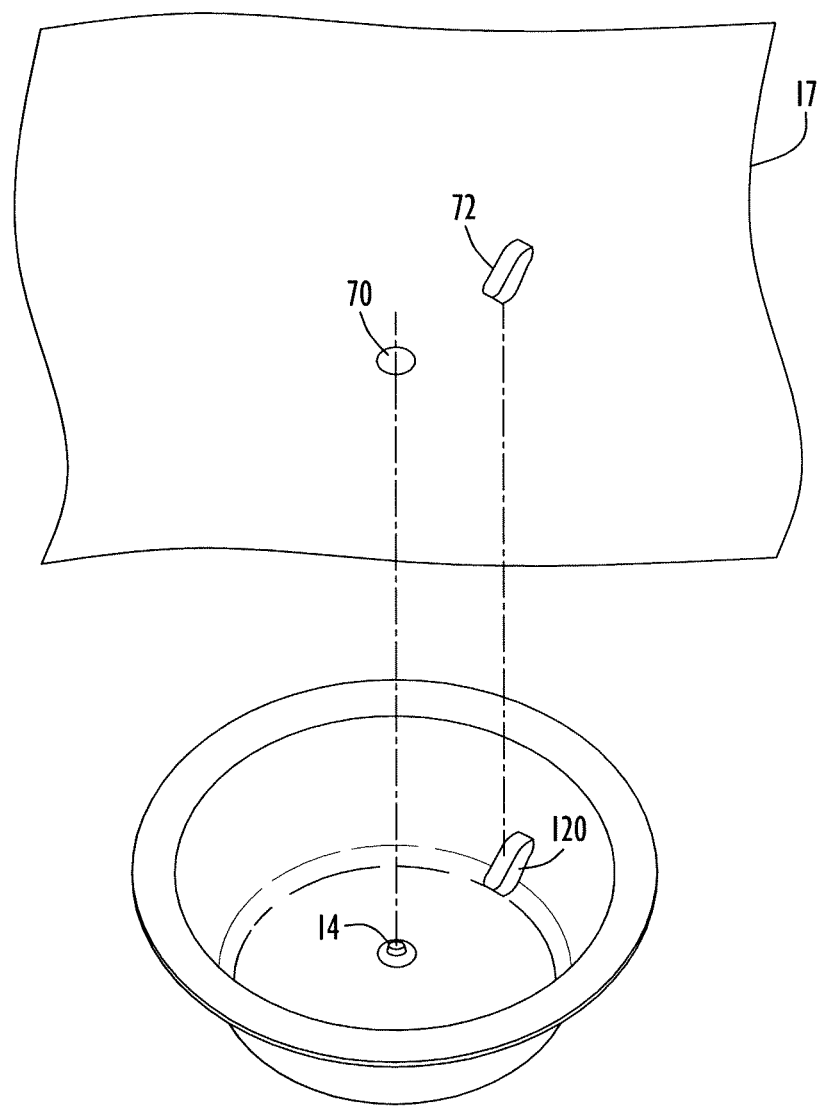
FIG. 8 is an exploded view in perspective of a surgical drape securable to and for use within the basin of FIG. 2 according to an embodiment of the present invention.

Surgical drapes may further be utilized in combination with basin 4 (without drape 10) to heat sterile fluid within drape containers. In this case, a drape is secured to the basin with a portion of the drape conforming to the basin interior to form a drape container for sterile fluid. The basin actuates limit switch 6, 7 as described above to enable heating of the sterile fluid in the drape container. A drape for use with basin 4 according to an embodiment of the present invention is illustrated in FIG. 8. Specifically, drape 17 is substantially similar to drape 15 described above for FIG. 6B and includes a well secure member 70 and a channel secure member 72. Well secure member 70 is preferably configured in the form of a generally semi-spherical dome to engage well 14 of basin 4. The well secure member is constructed of a substantially flexible or resilient material and includes dimensions suitable to enable a snap or friction fit engagement of the well member. The channel secure member is preferably in the form of a semi-cylindrical tubular member and constructed of a substantially flexible or resilient material. The channel secure member includes dimensions suitable to enable a snap or friction fit engagement of the alignment channel. The well and channel secure members further protect the drape from puncture by well 4 and alignment channel 120, and may serve to indicate the orientation or alignment of the drape over the fluid warming system.

The well and channel secure members may further include fastening devices (e.g., clips, etc.) to enable attachment of these members to the well and alignment channel. Secure members 70, 72 may be disposed on the drape sterile (e.g., engaging the well and alignment channel through the drape) and/or non-sterile (e.g., directly engaging the well and alignment channel) surfaces at locations enabling formation of a drape container within basin 4 and respective engagement of the well and alignment channel to secure the drape to the basin. The well and channel secure members may be attached or integrated into the drape by any conventional or other techniques (e.g., adhesion, heat welding, RF, etc.).

Drape 17 is made from a material that is impervious to the sterile fluid and sufficiently soft and flexible to conform to the basin walls. The thickness of the drape is preferably minimized to render thermal transfer therethrough most efficient, yet the thickness is sufficient to resist tearing and puncturing during normal use. The drape may be made of materials commonly used in hospitals for surgical drapes and is relatively thin to enable thermocouple 16 to measure temperature of the sterile fluid through the drape (and basin), and to enable heater 12 to heat the sterile fluid in the drape container. By way of example only, the drape has a thickness of approximately 2.0 to 4.0 mils. However, the drape may have any desired thickness. Drape 17 may also be made of polyurethane film as disclosed for the drape in aforementioned U.S.

Pat. No. 4,934,152 (Templeton). In addition, the drape may include sensors to detect the presence or absence of liquid within the receptacle and/or the presence of a drape leak. Examples of these types of drapes are disclosed in aforementioned U.S. Pat. No. 6,810,881 (Faries, Jr. et al.), U.S. Pat. No. 6,910,485 (Faries, Jr. et al.) and U.S. Pat. No. 7,176,030 (Faries, Jr. et al.).

In operation, drape 17 may be placed over the fluid warming system and within basin 4 to form a drape container. The drape is positioned within the basin to enable well secure member 70 to engage well 14 and channel secure member 72 to engage alignment channel 120 to secure the drape to the basin. Sterile fluid is placed within the drape container to be warmed by fluid warming system 100 (FIG. 1). Basin 4 actuates limit switch 6,7 as described above to enable heater 12 to heat the basin and drape container, while thermocouple 16 is received in well 14 to measure temperature of the sterile fluid.

Figure 9:
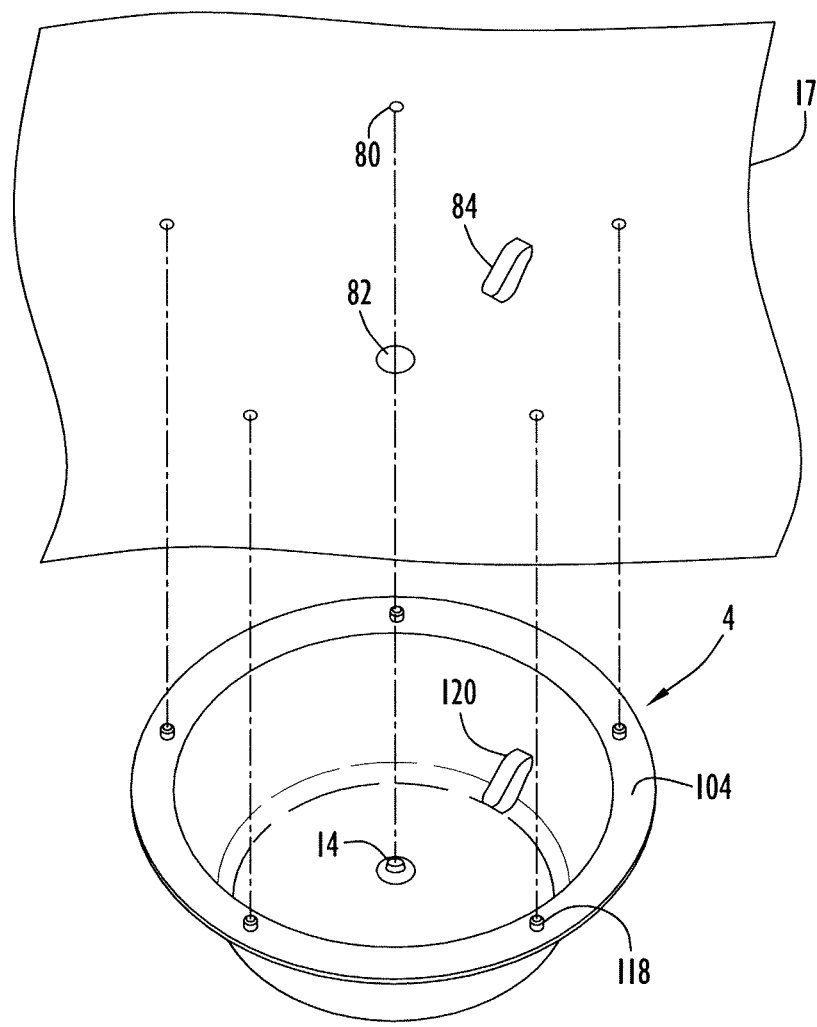
FIG. 9 is an exploded view in perspective of a surgical drape including fasteners to secure the drape to the basin of FIG. 2 according to an embodiment of the present invention.

Drape 17 may further engage posts 118 of basin 4 for use with fluid warming system 100 according to an embodiment of the present invention as illustrated in FIG. 9. Initially, drape 17 is substantially similar to the drape described above for FIG. 8 and includes a series of fasteners 80 preferably disposed on the non-sterile surface of the drape. The fasteners are generally cylindrical and include dimensions comparable to posts 118 of basin 4 to enable the fasteners to engage the posts in a snap or friction fit engagement. Fasteners 80 are disposed on the drape at locations substantially coincident corresponding posts 118 after enabling formation of a drape container within basin 4. A well cover member 82 is disposed on the drape non-sterile surface to cover well 14 of basin 4 and protect drape 17. Well cover member 82 may be generally semi-spherical to cover well 14, and is preferably constructed of suitable durable materials typically impervious to puncture by the basin well. The drape may further include a channel cover member 84 disposed on the non-sterile surface to cover alignment channel 120 of basin 4 and protect drape 17. Channel cover member 84 may be generally semi-cylindrical and is preferably constructed of suitable durable materials typically impervious to puncture by the alignment channel. The well and channel cover members protect the drape from puncture by well 14 and alignment channel 120, and may further serve (e.g., along with fasteners 80) to indicate the orientation or alignment of the drape over the fluid warming system.

In operation, drape 17 may be placed over the fluid warming system and within basin 4 to form a drape container. The drape is positioned within the basin to enable fasteners 80 to engage corresponding posts 118 to secure the drape to the basin and to enable well and channel cover members 82, 84 to cover well 14 and alignment channel 120 and protect the drape. Sterile fluid is placed within the drape container to be warmed by fluid warming system 100 (FIG. 1). Basin 4 actuates limit switch 6, 7 and receives thermocouple 16 within well 14 to enable heater 12 to heat the basin and drape container and to measure temperature of the sterile fluid as described above. Alternatively, the well and channel cover members and fasteners may be disposed on the sterile or any combination of the sterile and non-sterile surfaces to enable heating of the sterile fluid in substantially the same manner described above.

Figure 10:
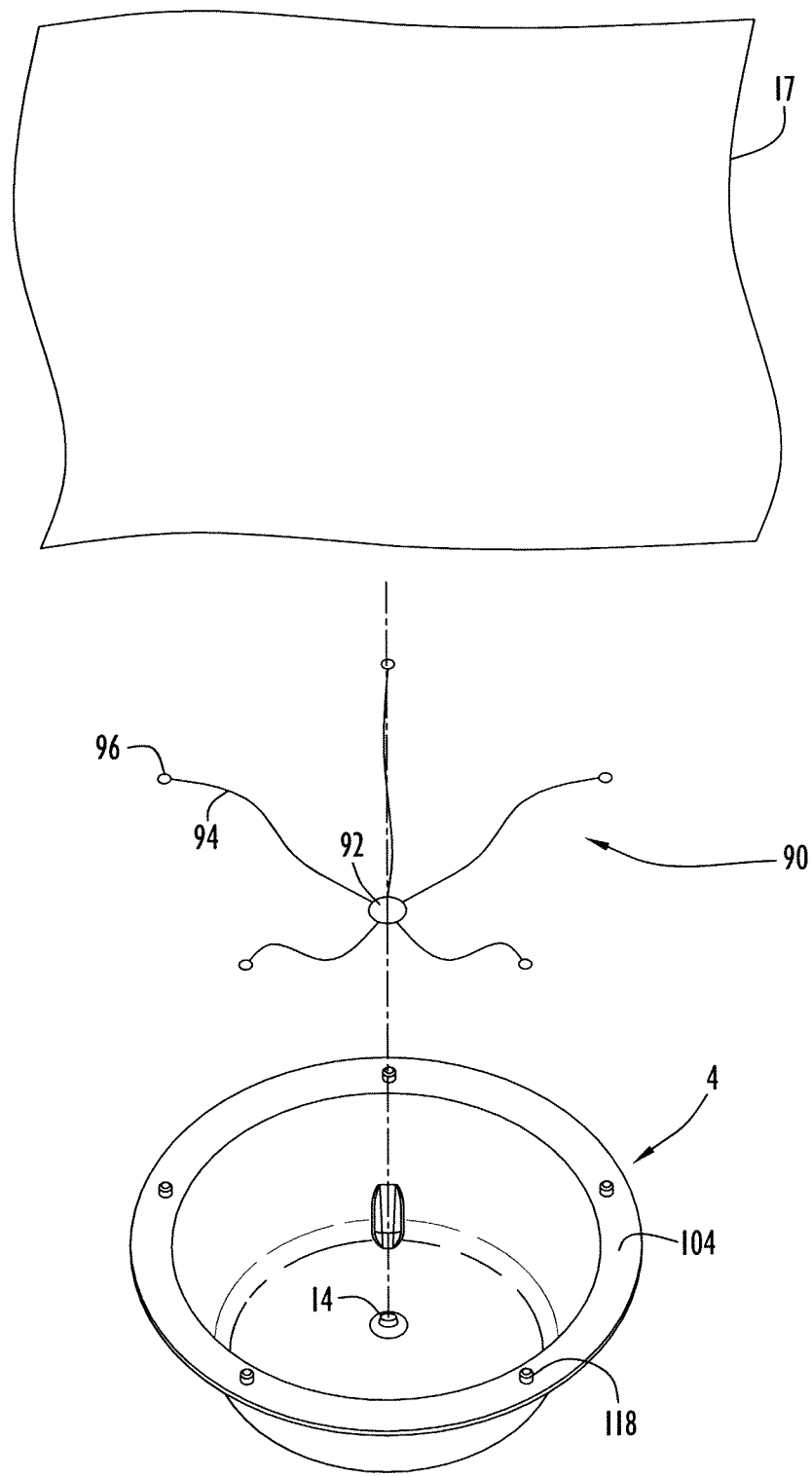
FIG. 10 is an exploded view in perspective of an engagement member enabling a surgical drape to be utilized with the basin of FIG. 2 according to an embodiment of the present invention.

An engagement member may be utilized to engage basin 4 and enable use of a drape with fluid warming system 100 (without drape 10) according to an embodiment of the present invention as illustrated in FIG. 10. Specifically, an engagement member 90 includes a generally hub and spoke or star type configuration with a well cover member 92 and a plurality of basin fasteners 96 coupled to well cover member 92 by a series of arms 94. Well cover member 92 is generally semi-spherical to cover well 14 of basin 4, and is preferably constructed of suitably durable materials typically impervious to puncture by the basin well. Well cover member 92 is typically disposed over well 14 at the basin bottom. Arms 94 each include a generally 'S'-type configuration and are attached to well cover member 92. The arms each include a corresponding basin fastener 96 attached to an arm distal end, and extend from well cover member 92 along the basin bottom and sidewall to a corresponding post 118 on basin rim 104.

Basin fasteners 96 are generally cylindrical and include dimensions comparable to posts 118 to enable the basin fasteners to engage the posts in a snap or friction fit engagement to secure the engagement member to the basin. Once the engagement member is secured to the basin, a drape 17 may be disposed within the basin over the engagement member to form a drape container therein. Drape 17 may be substantially similar to the drape described above for FIG. 8 (e.g., without the well and channel secure members). Since the engagement member is disposed outside the sterile field (e.g., beneath the drape), the actuation member need not be sterilized for each use.

Engagement member 90 may further be attached to drape 17. In this case, portions of drape 17 may be attached to well cover member 92 and/or arms 94, thereby forming a drape container in the area collectively defined between the arms. The engagement member and formed drape container are placed in the basin with basin fasteners 96 engaging basin posts 118 to secure the drape to the basin. The well cover member protects the drape from puncture by well 14, while engagement member 90 may further serve to indicate the orientation or alignment of the drape over the fluid warming system. The engagement member may be attached or integrated into the drape by any conventional or other techniques (e.g., adhesion, heat welding, RF, etc.). The engagement member is preferably attached to the non-sterile drape surface. However, the engagement member may include a plurality of components attached to any combination of the sterile and non-sterile drape surfaces (e.g., mirrored components attached to opposing sterile and non-sterile drape surfaces and coupled to each other through the drape, etc.).

In operation, engagement member 90 may be secured to basin 4 by basin fasteners 96 engaging basin posts 118. Once the engagement member is secured to the basin, drape 17 may be disposed within the basin over the engagement member to form a drape container therein. In the case of engagement member 90 being attached to drape 17, the engagement member and formed drape container are placed in the basin with basin fasteners 96 engaging corresponding basin posts 118 to secure the drape to the basin. Sterile fluid is placed within the drape container to be warmed by fluid warming system 100 (FIG. 1). Basin 4 actuates limit switch 6, 7 as described above to enable heater 12 to heat the basin and drape container, while thermocouple 16 is received in well 14 to measure temperature of the sterile fluid.

Drapes 17 described above may further include a preformed container portion contoured to match the contour of the basin. The preformed container portion is typically thicker than the remaining portions of the drape in order to resist puncture and enable the container portion to maintain the shape of the receptacle. By way of example only, the container portion may be made of a heavy gauge polyethylene/ionomer resin blend having a thickness of approximately ten to sixteen mils. The percentage of ionomer resin in the blend is in the approximate range of forty to seventy percent. In this case, the preformed container portion includes well secure member 70, channel secure member 72, well cover member 82 and/or engagement member 90 in substantially the same manner described above. Drapes 17 described above are designed to be disposable after a single use and are provided presterilized and prepackaged in a manner to preserve their sterile state during storage.

It will be appreciated that the embodiments described above and illustrated in the drawings represent only a few of the many ways of implementing a method and apparatus for warming medical solutions in a thermal treatment system employing a removable basin.

The fluid warming system may include any quantity of heating and/or cooling receptacles and/or basins in any combinations for use with the drapes and/or actuation members. The drapes and actuation members may be utilized with the receptacle of any quantity, shape or size. The drapes and actuation members may be utilized with the removable basin of any quantity, shape or size, and including any quantity of structures (e.g., thermocouple well, alignment channel, etc.) of any quantity, shape or size and disposed at any locations. The drapes and actuation members may be utilized with any types of thermal treatment systems that may include any conventional or other heating and/or refrigeration units to thermally treat any type of sterile medium or other substance to any desired temperature (preferably to temperatures near (e.g., above, at or below) body temperature, such as temperatures in the approximate range of 60° F.-160° F.).

The drapes and actuation members may be utilized with thermocouples or temperature sensors implemented by any conventional or other temperature sensing device (e.g., infrared, RTD, etc.) and disposed at any location on or proximate the receptacle and/or removable basin or within the system.

The drapes may be of any size or shape, may include any suitable thickness (e.g., for thermal transfer to thermally treat and/or measure temperature of the fluid, etc.) and may be constructed of any suitable materials. The drapes are preferably transparent or translucent to facilitate manipulation of controls through the drape; however, these drapes may have any degree of transparency (e.g., including opaque). The drapes may be manipulated in any fashion with any portions of the drapes serving as a drape container within a corresponding system receptacle or basin. The drapes may be of sufficient size to accommodate and form drape containers within any quantity or types of thermal treatment system receptacles and/or basins.

The drapes and actuation members may be utilized with any conventional or other limit switches with any types of actuators. Actuation member 48 may be of any quantity, shape or size, may be constructed of any suitable materials and may have any weight sufficient to actuate the limit switch. The base may be of any quantity, shape or size and may be constructed of any suitable materials, while the base opening may be of any quantity, shape or size to receive a temperature sensor. The cover member may be of any quantity, shape or size and may be constructed of any suitable materials. The actuation member and corresponding components (e.g., base, cover member, etc.) may be attached to the drape at any desired locations on the sterile and/or non-sterile surfaces via any conventional or other techniques (e.g., adhesion, heat welding, RF, etc.).

The plate may be of any quantity, shape or size, and may be constructed of any suitable materials. The plate channel may be of any quantity, shape or size, may be defined at any suitable locations and may be of any length suitable to receive the thermocouple. The plate opening may be of any quantity, shape or size and may be defined at any suitable locations, while the cover member may be attached to the plate at any desired locations via any conventional or other techniques (e.g., adhesion, heat welding, RF, etc.). The plate may be attached to the drape at any desired locations on the sterile and/or non-sterile surfaces via any conventional or other techniques (e.g., adhesion, heat welding, RF, etc.).

Actuation member 44 may be of any quantity, shape or size, may be constructed of any suitable materials and may have any weight sufficient to actuate the limit switch. The body may be of any quantity, shape or size and may be constructed of any suitable materials, while the body opening may be of any quantity shape or size to receive a temperature sensor. The sensor receptacle may be of any quantity, shape or size. The cover member may be of any quantity, shape or size and may be constructed of any suitable materials. The plate may be of any quantity, shape or size, and may be constructed of any suitable materials. The plate channel may be of any quantity, shape or size, may be defined at any suitable locations and may be of any length suitable to receive the thermocouple. The foot may be of any quantity, shape or size and may be constructed of any suitable materials. The plate opening may be of any quantity, shape or size and may be defined at any suitable locations, while the cover member may be attached to the plate at any desired locations. The sensor receptacle and components (e.g., actuation member body, cover member, foot, etc.) may be attached to the plate at any desired locations via any conventional or other techniques (e.g., adhesion, heat welding, RF, etc.). Further, the sensor receptacle and components (e.g., actuation member body, cover member, plate, foot, etc.) may be attached to the drape at any desired locations on the sterile and/or non-sterile surfaces via any conventional or other techniques (e.g., adhesion, heat welding, RF, etc.).

The well and channel secure members may be of any quantity, shape or size, may be constructed of any suitable materials, and may be attached to the drape at any desired locations on the sterile and/or non-sterile surfaces via any conventional or other techniques (e.g., adhesion, heat welding, RF, etc.). The secure members may be configured to engage any suitable basin portions (e.g., thermocouple well, alignment channel, etc.). The fasteners may be of any quantity, shape or size, may be constructed of any suitable materials, and may be attached to the drape at any locations on the sterile and/or non-sterile surfaces via any conventional or other techniques (e.g., adhesion, heat welding, RF, etc.). The fasteners may be configured to engage any portions of the receptacle and/or basin (e.g., posts, rim, etc.).

The engagement mechanism may be of any quantity, shape or size, and may be constructed of any suitable materials. The well cover member may be of any quantity, shape or size and may be constructed of any suitable materials. The arms may be of any quantity, shape or size, may include any configuration (e.g., 'S'-type, curved, linear, etc.), and may be constructed of any suitable materials. The basin fasteners may be of any quantity, shape or size, may be constructed of any suitable materials and may be disposed at any locations on the arms. The basin fasteners may be configured to engage any portions of the receptacle and/or basin (e.g., posts, rim, etc.). The engagement mechanism may be attached to the drape at any locations on the sterile and/or non-sterile surfaces via any conventional or other techniques (e.g., adhesion, heat welding, RF, etc.).

It is to be understood that the terms "top", "bottom", "front", "rear", "side", "height", "length", "width", "upper", "lower", "vertical" and the like are used herein merely to describe points of reference and do not limit the present invention to any particular orientation or configuration.

The present invention drapes and actuation members are not limited to the applications or systems described herein, but may be utilized for any types of thermal treatments systems to thermally treat any medical or other items (e.g., IV or other medical solutions (e.g., blood, pharmaceuticals or medication, etc.), containers, etc.).

From the foregoing description, it will be appreciated that the invention makes available a novel method and apparatus for warming medical solutions in a thermal treatment system employing a removable basin, where drapes and engaging structure are provided to facilitate use of a drape with the thermal treatment without use of the removable basin or engaging the drape with respect to the basin during use of the thermal treatment system.

Having described preferred embodiments of a new and improved method and apparatus for warming medical solutions in a thermal treatment system employing a removable basin, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A thermal treatment system comprising:
a receptacle;
a heater to heat items placed within the receptacle;
a limit switch that is operable to activate the heater upon identification of an item being placed within the receptacle; and
a drape device comprising:
a drape comprising a flexible material that conforms to at least a portion of the receptacle upon being placed within the receptacle of the thermal treatment system, wherein the drape includes a drape container to receive and retain fluids and other items within the receptacle, and provides a barrier between items placed in the drape container and the receptacle; and
an engaging structure coincident the drape container and configured to engage the drape and actuate the limit switch for activation of the heater when the drape device is positioned on the thermal treatment system and at least one item is placed on the drape within the receptacle, wherein the limit switch of the thermal treatment system includes an elongated member that protrudes into the receptacle, and the engaging structure comprises an actuation member configured to engage the limit switch when the actuation member is placed within the receptacle of the thermal treatment system so as to facilitate activation of the heater, and wherein the actuation member comprises a plate, and the plate includes a channel to receive the elongated member of the limit switch when the actuation member engages the limit switch;
wherein the drape includes a first surface upon which fluid and other items are placed and a second surface that engages the actuation member and portions of the receptacle of the thermal treatment system, a first surface of the plate is secured to the second surface of the drape, and the plate includes a foot attached to a second surface of the plate at a selected distance from the channel so as to facilitate, a substantially level orientation of the plate with respect to the receptacle of the thermal treatment system when the actuation member engages with the limit switch.

2. A drape device for use with a thermal treatment system comprising:
a thermal treatment comprising:
a receptacle dimensioned to receive a basin;
heater to heat items placed within the receptacle; and
a limit switch that is operable to identify when the basin or other item is placed within the receptacle and to further activate the heater upon identification by the limit switch of the basin or other item being placed within the receptacle; and
a drape device comprising:
a drape comprising a flexible material that conforms to at least a portion of the receptacle upon being placed within the receptacle of the thermal treatment system, wherein the drape is further configured to receive and retain fluids and other items within the receptacle and to provide a harrier between items placed on the drape and the receptacle; and
an engaging structure configured to engage the drape and the basin so as to facilitate operation of the limit switch and activation of the heater when the drape device is positioned on the thermal treatment system and at least one item is placed on the drape within the receptacle, wherein the engaging structure is configured to engage with the basin of the thermal treatment system and the drape so as to secure the drape within the basin during operation of the thermal treatment system, and wherein the basin includes a rim disposed at an upper edge of the basin and a plurality of posts disposed at spaced locations along the rim, and the engaging structure comprises fasteners that are securable to the posts in a friction fit engagement.

3. The device of claim 2, wherein the fasteners are attached to the drape so as to releasably secure the drape to the basin.

4. The device of claim 2, wherein the limit switch of the thermal treatment system includes an elongated member that protrudes into the receptacle, the basin includes a well disposed along an outer bottom wall surface of the basin that receives and engages with the elongated member so as to facilitate activation of the heater when the basin is provided within the receptacle, the engaging structure further comprises a well secure structure and a plurality of elongated arms extending from the well secure structure, the well secure structure is configured to engage with an interior protruding bottom wall surface portion of the basin that defines the well, and the well secure structure is further connected to each fastener via an elongated arm.

5. The device of claim 4, wherein the well secure structure and fasteners are attached to the drape.

6. A thermal treatment system comprising:
a receptacle;
a heater to heat items placed within the receptacle;
a limit switch that is operable to identify when an item is placed within the receptacle and to further activate the heater upon identification by the limit switch of the item being placed within the receptacle, wherein the limit switch includes an elongated member that protrudes into the receptacle; and
a drape device comprising:
a drape comprising a flexible material that conforms to the receptacle to form a drape container therein upon being placed within the receptacle of the thermal treatment system, wherein the drape container receives and retains fluids and other items within the receptacle, and the drape provides a barrier between items placed in the drape container and the receptacle; and
an engaging structure coincident the drape container and configured to engage the drape and contact and apply forces to the limit switch to actuate the limit switch for activation of the heater to apply heat to the drape container when the drape device is positioned on the thermal treatment system and at least one item is placed on the drape within the receptacle.

7. The system of claim 6, wherein the elongated member of the limit switch comprises a temperature sensor that provides measured temperature information to the system in relation to the temperature of items within the receptacle.

8. The system of claim 6, wherein the engaging structure comprises an actuation member configured to engage the limit switch when the actuation member is placed within the receptacle of the thermal treatment system so as to facilitate activation of the heater.

9. The system of claim 8, wherein the actuation member comprises an annular member that fits around the elongated member of the limit switch.

10. The system of claim 9, wherein the actuation member further comprises a cover member attached to the annular member and includes an opening that facilitates receipt of the elongated member within the cover member when the annular member is fit around the elongated member.

11. The system of claim 10, wherein at least one of the annular member and cover member is attached to the drape.

12. The system of claim 10, wherein the drape includes an opening through which the cover member protrudes.

13. The system of claim 9, wherein the drape includes a first surface upon which fluid and other items are placed and a second surface that engages the actuation member and portions of the receptacle of the thermal treatment system, and the second surface of the drape includes a sensor receptacle to engage the elongated member of the limit switch when the drape is placed within the receptacle of the thermal treatment system.

14. The system of claim 8, wherein the actuation member comprises a plate, and the plate includes a channel to receive the elongated member of the limit switch when the actuation member engages the limit switch.

15. The system of claim 8, wherein the actuation member comprises a cover member including an opening to facilitate receipt of the elongated member of the limit switch within the cover member when the actuation member engages the limit switch.

16. The system of claim 15, wherein the cover member is attached to the drape.

17. The system of claim 8, wherein the actuation member is secured to the drape.

18. A thermal treatment system comprising:
a receptacle dimensioned to receive a removable basin;
a heater to heat items placed within the receptacle;
a limit switch that is operable to identify when an item is placed within the receptacle and to further activate the heater upon identification by the limit switch of the item being placed within the receptacle, wherein the limit switch includes an elongated member that protrudes into the receptacle and the basin includes a well disposed along an outer bottom wall surface of the basin that receives and engages with the elongated member so as to facilitate activation of the heater when the basin is provided within the receptacle; and
a drape device comprising:
 a drape comprising a flexible material that conforms to at least a portion of the receptacle upon being placed within the receptacle of the thermal treatment system, wherein the drape includes a drape container to receive and retain fluids and other items within the receptacle, and provides a barrier between items placed on the drape and the receptacle; and
 an engaging structure coincident the drape container and configured to engage the drape when the drape device is positioned on the thermal treatment system, wherein the engaging structure is configured to engage with an interior surface of a bottom portion of the basin of the thermal treatment system and the drape so as to secure the drape within the basin interior during operation of the thermal treatment system, and wherein the engaging structure comprises a well secure structure disposed on a surface of the drape that engages with an interior protruding bottom wall surface portion of the basin that defines the well.

19. The thermal treatment system of claim 18, wherein the basin includes an alignment channel section disposed on an interior surface of the basin that facilitates a selected alignment of the basin within the receptacle of the thermal treatment system, and the engaging structure comprises a securing member attached to the drape that engages with the alignment channel section of the basin.

20. A method of thermally treating items utilizing a thermal treatment system and a drape device, the thermal treatment system comprising a receptacle, a heater to heat items placed within the receptacle and a limit switch that is operable to activate the heater upon identification of an item being placed within the receptacle, the limit switch including an elongated member that protrudes into the receptacle, the drape device comprising a drape and engaging structure, the drape comprising a flexible material, wherein the method comprises:
 (a) receiving the drape and the engaging structure within the receptacle of the thermal treatment system such that the drape engages the engaging structure, wherein the drape conforms to the receptacle to form a drape container therein to receive and retain fluids and other items, and provides a barrier between items placed in the drape container and the receptacle, and wherein the engaging structure is coincident the drape container and configured to engage the drape and contact and apply forces to the limit switch to actuate the limit switch for activation of the heater; and
 (b) receiving at least one item in the drape container within the receptacle so as to thermally treat the drape container and the at least one item upon operation of the limit switch and activation of the heater.

21. The method of claim 20, wherein the elongated member of the limit switch comprises a temperature sensor, and the method further comprises:
 (c) providing measured temperature information to the system, via the temperature sensor, wherein the measured temperature information represents the temperature of items disposed in the drape container within the receptacle.

22. A method of thermally treating items utilizing a thermal treatment system and a drape device, the thermal treatment system comprising a receptacle, a heater to heat items placed within the receptacle and a limit switch that is operable to identify when a basin or other item is placed within the receptacle and to further activate the heater upon identification by the limit switch of the basin or other item being placed within the receptacle, the limit switch including an elongated member that protrudes into the receptacle, the drape device comprising a drape and engaging structure, the drape comprising a flexible material, wherein the method comprises:
 (a) receiving the engaging structure within the thermal treatment system such that the engaging structure engages the receptacle, wherein the engaging structure comprises an actuation member, and step (a) further comprises:
  (a.1) receiving the actuation member within the receptacle such that the actuation member engages the limit switch, wherein engagement of the actuation member with the limit switch facilitates activation of the heater;

(b) receiving the drape within the receptacle of the thermal treatment system such that the drape engages the engaging structure, wherein the drape within the receptacle is configured to receive and retain fluids and other items and to provide a barrier between items placed on the drape and the receptacle; and (c) receiving at least one item on the drape within the receptacle so as to thermally treat the at least one item upon operation of the limit switch and activation of the heater.

23. The method of claim 22, wherein the actuation member is secured to the drape.

24. The method of claim 22, wherein the actuation member is not secured to the drape, and step (a) occurs before step (b).

25. The method of claim 22, wherein the actuation member is not secured to the drape, and step (b) occurs before step (a) such that the drape is disposed between the actuation member and the receptacle.

26. The method of claim 22, wherein the actuation member comprises an annular member, and step (a.1) further comprises:

(a.1.1) securing the annular member around the elongated member of the limit switch.

27. The method of claim 22, wherein the actuation member comprises a plate, and step (a.1) further comprises:

(a.1.1) engaging the elongated member of the limit switch with a channel of the plate.

28. The method of claim 22, wherein the actuation member comprises a cover member including an opening to facilitate receipt of the elongated member of the limit switch, and step (a.1) further comprises:

(a.1.1) securing the cover member over the elongated member of the limit switch.

29. A method of thermally treating items utilizing a thermal treatment system employing a removable basin and a drape device, the thermal treatment system comprising a receptacle to receive the basin, a heater to heat items placed within the receptacle and a limit switch that is operable to activate the heater upon identification of an item being placed within the receptacle, the limit switch including an elongated member that protrudes into the receptacle, the drape device comprising a drape and engaging structure, the drape comprising a flexible material, wherein the method comprises:

(a) receiving the engaging structure within the thermal treatment system such that the engaging structure engages the basin, wherein step (a) further comprises:

(a.1) securing the engaging structure to an interior surface of a bottom portion of the basin after the basin is provided within the receptacle;

(b) receiving the drape within the basin of the thermal treatment system such that the drape engages the engaging structure, wherein the drape within the basin includes a drape container to receive and retain fluids and other items, and provides a barrier between items placed on the drape and the basin, and wherein the engaging structure is coincident the drape container; and (c) receiving at least one item on the drape within the basin so as to thermally treat the at least one item upon operation of the limit switch and activation of the heater.

30. The method of claim 29, wherein the basin includes a well disposed along an outer bottom wall surface of the basin that receives and engages with the elongated member so as to facilitate activation of the heater when the basin is provided within the receptacle, the well of the basin forming an interior protruding bottom wall surface portion within the basin, the engaging structure comprises a well secure structure disposed on a surface of the drape, and step (a.1) further comprises:

(a.1.1) securing the well secure structure of the drape to the interior protruding bottom wall surface portion of the basin.

31. The method of claim 29, wherein the basin includes an alignment channel section disposed on an interior surface of the basin that facilitates a selected alignment of the basin within the receptacle of the thermal treatment system, the engaging structure comprises a securing member attached to the drape, and step (a.1) further comprises:

(a.1.1) securing the securing member of the drape to the alignment channel section of the basin.

32. A method of thermally treating items utilizing a thermal treatment system and a drape device, the thermal treatment system comprising a receptacle dimensioned to receive a basin, a heater to heat items placed within the receptacle and a limit switch that is operable to identify when the basin or other item is placed within the receptacle and to further activate the heater upon identification by the limit switch of the basin or other item being placed within the receptacle, the limit switch including an elongated member that protrudes into the receptacle and comprises a temperature sensor, the drape device comprising a drape and engaging structure, the drape comprising a flexible material, wherein the method comprises:

(a) receiving the engaging structure within the thermal treatment system, wherein the engaging structure is configured to engage with the basin of the thermal treatment system, and step (a) further comprises:

(a.1) securing the engaging structure to the basin after the basin is provided within the receptacle, and wherein the basin includes a rim disposed at an upper edge of the basin and a plurality of posts disposed at spaced locations along the rim, the engaging structure comprises fasteners that correspond with the posts, and step (a.1) further comprises:

(a.1.1) securing the fasteners of the engaging structure to the posts of the basin;

(b) receiving the drape within the basin of the thermal treatment system such that the drape engages the engaging structure, wherein the drape installed within the basin is configured to receive and retain fluids and other items and to provide a barrier between items placed on the drape and the basin;

(c) receiving at least one item on the drape within the basin so as to thermally treat the at least one item upon operation of the limit switch and activation of the heater; and (d) providing measured temperature information to the system, via the temperature sensor, wherein the measured temperature information represents the temperature of items disposed on the drape within the basin.

33. The method of claim 32, wherein the fasteners are attached to the drape.

34. The method of claim 32, wherein the basin includes a well disposed along an outer bottom wall surface of the basin that receives and engages with the elongated member so as to facilitate activation of the heater when the basin is provided within the receptacle, the well of the basin forming an interior protruding bottom wall surface portion within the basin, the engaging structure further comprises a well secure structure and a plurality of elongated arms, the well secure structure separately connects with each fastener via an elongated arm, and step (a1.1) further comprises:

(a.1.1.1) securing the well secure structure of the engaging structure to the interior protruding bottom wall surface portion of the basin.

35. The method of claim 34, wherein the well secure structure and the fasteners are attached to the drape.

\* \* \* \* \*